United States Patent
Chen

(10) Patent No.: US 9,499,529 B2
(45) Date of Patent: Nov. 22, 2016

(54) THERAPEUTIC USES OF CURCUMIN ANALOGS FOR TREATMENT OF PROSTATE CANCER

(71) Applicant: California State University Fresno, Fresno, CA (US)

(72) Inventor: Qiao-Hong Chen, Fresno, CA (US)

(73) Assignee: California State University, Fresno, Fresno, CA (US)

( * ) Notice: Subject to any disclaimer, the term of this patent is extended or adjusted under 35 U.S.C. 154(b) by 19 days.

(21) Appl. No.: 14/318,295

(22) Filed: Jun. 27, 2014

(65) Prior Publication Data

US 2015/0017720 A1   Jan. 15, 2015

Related U.S. Application Data

(60) Provisional application No. 61/842,100, filed on Jul. 2, 2013, provisional application No. 61/894,314, filed on Oct. 22, 2013, provisional application No. 61/894,338, filed on Oct. 22, 2013.

(51) Int. Cl.

| | |
|---|---|
| *C07D 403/06* | (2006.01) |
| *C07D 413/06* | (2006.01) |
| *C07D 417/06* | (2006.01) |
| *C07D 413/14* | (2006.01) |
| *C07D 413/08* | (2006.01) |

(52) U.S. Cl.
CPC ........... *C07D 413/14* (2013.01); *C07D 403/06* (2013.01); *C07D 413/06* (2013.01); *C07D 413/08* (2013.01); *C07D 417/06* (2013.01)

(58) Field of Classification Search
CPC . C07D 403/06; C07D 413/06; C07D 417/06
See application file for complete search history.

(56) References Cited

U.S. PATENT DOCUMENTS

| 2012/0288555 A1 | 11/2012 | Awasthi et al. |
| 2014/0051742 A1 | 2/2014 | Nwualia |

FOREIGN PATENT DOCUMENTS

| CN | 101475532 A | * | 7/2009 |
| CN | 101723935 A | * | 6/2010 |

OTHER PUBLICATIONS

Wei et al. Oncology Letters, 2012, vol. 4, pp. 279-284 (Published Online May 12, 2012).*
Abonia et al. European Journal of Medicinal Chemistry, 2012, vol. 57, pp. 29-40 (Published Online Sep. 6, 2012).*
American Cancer Society, What are the key statistics about prostate cancer? Website. http://www.cancer.org/cancer/prostatecancer/detailedguide/prostate-cancer-key-statistics. Jun. 30, 2014.
Aggarwal, B., et al. Anticancer Potential of Curcumin. Preclinical and Clinical Studies. Anticancer Research 23: 363-98. 2003.
Chaturvedi, M., et al. NF-jB addiction and its role in cancer: 'one size does not fit all'. Oncogene 30: 1615-1630. 2011.
Aggarwal, B. Prostate cancer and curcumin: Add spice to your life. Cancer Biology & Therapy 7:9, 1436-1440 Sep. 2008.
Teiten, M-H., et al. Chemopreventive potential of curcumin in prostate cancer. Genes Nutr 5:61-74. 2010.
Zimmerman, G., et al. Multi-target therapeutics: when the whole is greater than the sum of the parts. Drug Discovery Today 12:(1/2), 34-42. Jan. 2007.
Brown, A., et al. Monocarbonyl Curcumin Analogues: Heterocyclic Pleiotropic Kinase Inhibitors That Mediate Anticancer Properties. J. Med. Chem. 56: 3456-3466, 2013.
Sharma, R., et al. Phase 1 Clinical Trial of Oral Curcumin: Biomarkers of Systematic Activity and Compliance. Clin Cancer Res. 10: 6847-6854. 2004.
Zhou, H., et al. Targets of curcumin. Curr Drug Targets. 12(3): 332-347. 2011.
Anand, P., et al. Bioavailability of Curcumin: Problems and Promises, Mol. Pharm. 4(6): 807-818, 2007.
Garcea, G., et al. Detection of curcumin and its metabolites in hepatic tissue and portal blood of patients following oral administration. Brit. J. Cancer 90: 1011-1015, 2004.
Lee, K-H. Discovery and Development of Natural Product-Derived Chemotherapeutic Agents Based on a Medicinal Chemistry Approach, J. Nat. Prod. 73: 500-516. 2010.
Lin, L, et al. New curcumin analogues exhibit enhanced growth-suppressive activity and inhibit AKT and signal transducer and activator of transcription 3 phosphorylation in breast and prostate cancer cells. Cancer Sci. 100(9): 1719-1727. 2009.
Parkin, M., et al. Global Cancer Statistics, 2002. CA Cancer J Clin. 55:74-108. 2005.
Silverman, RB. Drug discovery and development, The Organic Chemistry of Drug Design and Drug Action, 2nd Edition. Elsevier Academic Press. p. 32. 2004.
Yadav, B., et al. Synthesis and cytotoxic potential of heterocyclic cyclohexanone analogues of curcumin. Bioorganic & Medicinal Chemistry. 18: 6701-6707, 2010.
Seto, M., et al. Orally active CCR5 antagonists as anti-HIV-1 agents. Part 3: Synthesis and biological activities of 1-benzazepine derivatives containing a sulfoxide moiety. Bioorganic & Medicinal Chemistry. 13: 363-386. 2005.
Cao, B., et al. Synthesis of the pyridinyl analogues of dibenzylideneacetone (pyr-dba) via an improved Claisen-Schmidt condensation, displaying diverse biological activities as curcumin analogues. Org. Biomol. Chem.10: 1239-1245. 2012.
Sehnal, P., et al. Heteroaromatic Analogues of Dibenzylideneacetone (dba) and Pd0 2(het-dba)3 Complexes: Effect of a Thienyl Moiety on the Reactivity of Pd0($\eta$2-thn-dba)(PPh3)2/Pd0(PPh3)2 (n)1 or 2) and Pd0($\eta$2-th2-dba)(dppe)/Pd0(dppe) in Oxidative Addition Reactions with Iodobenzene. Organometallics. 28: 824-829. 2009.
Corbel, B, et al. An Efficient Synthesis of Dialkyl 2-oxoalkanephosphonates and diphenyl-2-oxoalkylphosphine oxides from 1-chloralkyl ketones. Synthesis. 11:1048-1051. 1985.

(Continued)

*Primary Examiner* — James D Anderson
(74) *Attorney, Agent, or Firm* — Grace Liu, Esq.

(57) ABSTRACT

This invention relates generally to methods of treating aggressive cancers, such as hormone-refractory metastatic prostate cancer, by exposing the aggressive cancer cells to curcumin analogs having the claimed structural scaffolds and side groups. The anticancer effects of curcumin are associated with its influence on numerous growth factors within the cells. However, its clinical development has been limited by its suboptimal pharmacokinetics and poor bioavailability caused by poor solubility in water and rapid in vivo metabolism. There is the need to develop new and improved curcumin analogs with better potency, water solubility, and in vivo metabolic stability, as well as retained safety profiles. Curcumin analogs having one of the claimed four novel scaffolds with basic heteroaromatic side groups show the ability to decrease aggressive cancer cell viability and to inhibit aggressive cancer cell growth.

5 Claims, 3 Drawing Sheets

(56) References Cited

OTHER PUBLICATIONS

Le, P., et al. A General Method for the Enantioselective Synthesis of r-Chiral Heterocycles. Org. Lett. 14(23) 6104-6107. 2012.

Van Loevezijin, A., et al. N0-(Arylsulfonyl)pyrazoline-1-carboxamidines as Novel, Neutral 5-Hydroxytryptamine 6 Receptor (5-HT6R) Antagonists with Unique Structural Features. J. Med. Chem, 54: 7030-7054. 2011.

Kania, R. Kinase Inhibitor Drugs, NY: John Wiley & Sons, Inc. Chapter 7: Structure Based Design and Characterization of Axitinib. pp. 167-201. 2009.

Samaan, N., et al. Design, synthesis, and evaluation of novel heteroaromatic analogs of curcumin as anti-cancer agents. Eur. J. Med. Chem. 75:123-131. 2014.

* cited by examiner

THERAPEUTIC USES OF CURCUMIN ANALOGS FOR TREATMENT OF PROSTATE CANCER

BACKGROUND OF THE INVENTION

1. Field of the Invention

This invention relates generally to methods of treating aggressive cancers, such as hormone-refractory metastatic prostate cancer, by exposing the aggressive cancer cells to curcumin analogs.

2. Description of the Related Prior Art

Prostate cancer has the highest incidence and the second highest cancer mortality in American men. The American Cancer Society estimates that 233,000 new cases of prostate cancer will be diagnosed and 29,480 men will die of prostate cancer in the United States in 2013 (American Cancer Society, 2014). Current therapies (radical prostatectomy, chemotherapy, local radiotherapy, or hormonotherapy) are successful in treating localized, androgen-dependent, prostate cancer. However, treatment of hormone-refractory prostate cancer remains hindered by inevitable progression of resistance to first-line treatment with docetaxel. Consequently, novel drugs are needed to treat advanced hormone-resistant prostate cancer (Feldman, et al., 2001; Corcoran, et al., 2012).

Curcumin or diferuloylmethane, a polyphenolic molecule extracted from the rhizome of the plant *Curcuma longa* (turmeric), is a yellow spice used as curry ingredient and has been used for centuries in Ayurvedic, Chinese, and Hindu medicine systems. There is a huge difference in the rate of incidence of prostate cancer between Western countries (120 prostate cancer incidents per 100,000 people in Northern America) and East Asian countries (less than 10 prostate cancer incidents per 100,000 people in Asia) (Lin, et al., 2005).

The increased risk of prostate cancer in the first generation of Asian men emigrating to the United States suggests a chemopreventive effect of Asian traditional food. Recent preclinical and clinical studies have demonstrated that curcumin has a number of anticancer properties (Aggarwal, et al., 2003; Chaturvedi, et al., 2011). The potential of curcumin to treat both androgen-dependent and androgen-independent prostate cancer has been demonstrated by the in vitro and in vivo studies (Aggarwal, 2008; Teiten, et al., 2010).

A new philosophy that favors multi-targeted drugs has recently gained momentum (Zimmerman, et al., 2007). Curcumin serves as a good example of a class of compounds that is able to target multiple enzymes with a "magic shotgun" (Brown, et al., 2013). The anticancer effects of curcumin are associated with its influence on numerous growth factors within the cell (Sharma, et al., 2004; Zhou, et al., 2011). The effect of curcumin on any particular growth factor is small, but its aggregate effect is significant. Curcumin's aggregate effects are especially valuable for diseases like cancer that are complex, inflammation associated, and often involve mutations in multiple genes. Because of its potential ability to treat hormone-refractory prostate cancer, its low molecular weight, lack of toxicity, and its mechanism of action against multiple targets, curcumin could be an ideal candidate as an androgen-independent agent against prostate cancer.

However, its clinical development has been limited by its suboptimal pharmacokinetics and poor bioavailability caused by poor solubility in water and rapid in vivo metabolism (Anand, et al., 2007). It has been found that, with oral administration at the dose of 450 mg-3600 mg/day in a phase I trial, the blood concentration of curcumin in plasma and target tissues falls under the detection limit (Garcea, et al., 2004). Curcumin has been used as a lead compound to design and synthesize analogs for the potential treatment of prostate cancer. Some analogs, such as JC-22 (Lee, 2010), FLLL11, and FLLL12 (Lin et al., 2009) were found to be more potent than curcumin towards PC-3 prostate cancer cell line.

Curcumin analogs also have promise as HIV and neurodegenerative treatment agents (US Pat. Pub No. 2014/0051742 A1) by showing anti-retroviral, neuroprotective, anti-glucosidase, and anti-HIV integrase properties. Curcumin analogs have shown anti-proliferative activity in tumor cells (US Pat. Pub No. 2012/0288555).

However, all of the curcumin analogs disclosed in the prior art have low bioavailability due to poor water solubility or suboptimal potency. There is the need to develop new and improved curcumin analogs with better potency, water solubility, and greater in vivo metabolic stability, as well as retained safety profiles.

SUMMARY OF THE INVENTION

The claimed invention is a method for decreasing the viability of aggressive mammalian cancer cells and inhibiting growth of the aggressive mammalian cancer cells, comprising administering an effective amount of at least one curcumin analog having a scaffold represented by one of general formulas (I) to (IV) to the aggressive mammalian cancer cells:

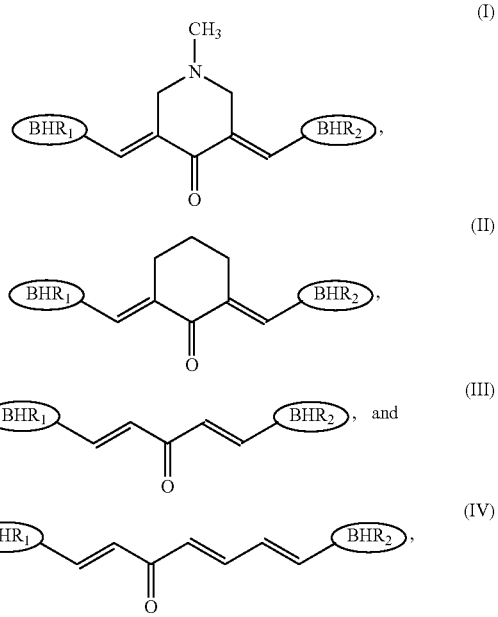

wherein each of $BHR_1$ and $BHR_2$ independently is a basic heteroaromatic ring group. In one aspect of the invention, the $BHR_1$ and the $BHR_2$ independently may be a five membered basic heteroaromatic ring group, a six membered basic heteroaromatic ring group, or a bulky heteroaromatic ring group. In another aspect of the invention, the $BHR_1$ and said $BHR_2$ independently may be a side group selected from the group of compounds listed in Table 1, Table 2, and Table 3, shown in the Specification. In one aspect of the invention, the scaffold is represented by general formula (III), and the BHR₁ and the BHR₂ both are

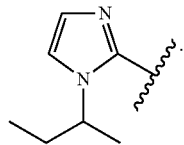

In another aspect of the invention, the scaffold is represented by general formula (III), and the BHR₁ and the BHR₂ both are

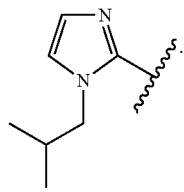

In another aspect of the invention, the scaffold is represented by general formula (III), and the BHR₁ and the BHR₂ both are

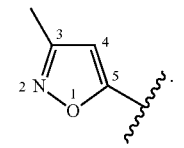

DETAILED DESCRIPTION OF THE INVENTION AND PREFERRED EMBODIMENTS

Figure 1:
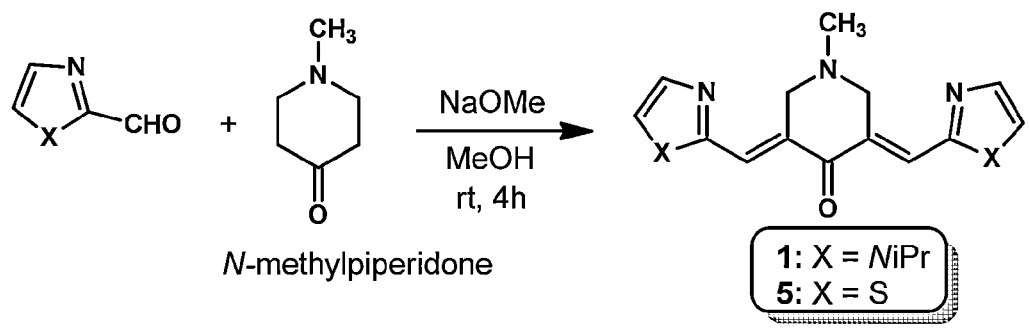
FIG. 1 shows a synthesis process to produce curcumin analogs having a scaffold represented by general formula (I).

The present invention relates to curcumin analog compounds and methods for decreasing the viability of aggressive cancer cells and inhibiting the growth of aggressive cancer cells, such as metastatic hormone-refractory prostate cancer cells.

The present invention relates to methods of decreasing the viability of aggressive cancer cells and inhibiting the growth of aggressive cancer cells by administering effective amounts of the curcumin analog compounds to the aggressive cancer cells. These compounds may have one of the following general formulas (I)-(IV):

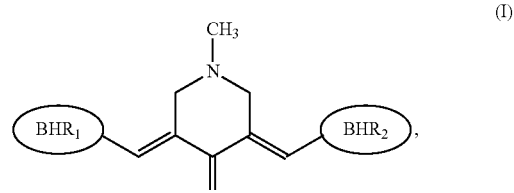

(I)

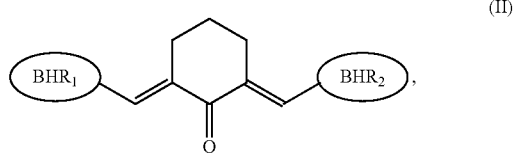

(II)

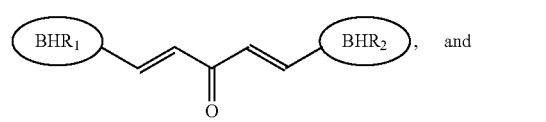

(III), and

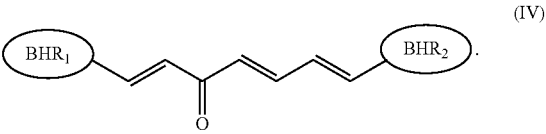

(IV)

A. DEFINITIONS

The term "decreasing" as used herein means to make something less according to a quantifiable measurement.

The term "inhibiting" as used herein means to provide a barrier to desired progress, and may be used interchangeably with the following: reducing, slowing, stopping, obstructing, impeding, and preventing.

The term "viability" as used herein means the ability of a living thing to stay alive.

The term "expression" as used herein defines the process of gene expression including one, some or all of the following steps: transcription, RNA splicing, RNA stabilization, translation, and post-translational modification.

The term "administering" as used herein may be used interchangeably with the following: exposed to, contacted with, passed over, incubated with, combined with, flowed over, and added to.

The term "effective amount" as used herein defines an amount of a given curcumin analog compound exposed to aggressive cancer cells which results in an objectively quantifiable reduction in viability of the cells and an objectively quantifiable reduction in the growth of the aggressive cancer cells as observed or noted by a scientist, clinician, or other qualified observer of ordinary skill in the art.

The term "aggressive cancer cells" as used herein defines cancer cells which grow quickly as defined by those of ordinary skill in the art and can spread beyond the area where the cells originated The term "independently" as used herein indicates that the $BHR_1$ and $BHR_2$ groups of general formulas (I)-(IV) can be identical or different. The $BHR_1$ and $BHR_2$ groups may both be 1-isopropyl-1H-imidazole-2-yl, or the $BHR_1$ group may be 1-isopropyl-1H-imidazole-2-yl and the $BHR_2$ group may be 2-methyloxazol-4-yl.

The term "BHR" means basic heteroaromatic ring.

The term "analog" means a compound having a structure similar to that of another one, but differing from it in respect of a certain component such as a functional group or a substructure. The term "analog" is used interchangeably with "analog compound."

B. CURCUMIN ANALOG SCAFFOLDS REPRESENTED BY GENERAL FORMULAS (I)-(IV)

Curcumin analogs are compounds that have a central monoketone linker bonded to two identical or different basic N-containing heteroaromatic rings. There are four general scaffolds of curcumin analog compounds consisting of different central monoketone linker: (3E,5E)-3,5-bis(heteroarylmethylene)-1-methylpiperidin-4-one (general formula (I)), (2E,6E)-2,6-bis(heteroarylmethylene) cyclohexanone (general formula (II)), (1E,4E)-1,5-bis(heteroaryl)penta-1,4-dien-3-one (general formula (III)), and (1E,4E,6E)-1,7-bis(heteroaryl)hepta-1,4,6-trien-3-one (general formula (IV)). The heteroaromatic group may independently be five membered, six membered, or a bulky basic nitrogen-containing heteroaromatic ring. The heteroaromatic ring may be substituted or unsubstituted. The substituent on the heteroaromatic ring may be C1-C6 saturated alkyl group, C3-C6 cycloalkyl group, —F, or $CF_3$.

For the scaffold represented by general formula (I), the curcumin analog compounds are characterized by a five carbon linker with 1-methylpiperidin-4-one as the central monoketone moiety and two terminal, basic nitrogen-containing heteroaromatic rings. The heteroaryl group may independently be five membered, six membered, or a bulky basic nitrogen-containing heteroaromatic ring. The heteroaromatic ring may be substituted or unsubstituted. The substituent on the heteroaromatic ring may be C1-C6 saturated alkyl group, C3-C6 cycloalkyl group, —F, or $CF_3$.

For the scaffold represented by general formula (II), the curcumin analog compounds are characterized by a five carbon linker with cyclohexanone as the central monoketone moiety and two terminal basic nitrogen-containing heteroaromatic rings. The heteroaromatic group may independently be a five membered, a six membered, or a bulky basic nitrogen-containing heteroaromatic ring. The heteroaromatic ring may be substituted or unsubstituted. The substituent on the heteroaromatic ring may be C1-C6 saturated alkyl group, C3-C6 cycloalkyl group, —F, or $CF_3$.

For the scaffold represented by general formula (III), the curcumin analog compounds are characterized by a five carbon linker with acetone as the central monoketone moiety and two terminal, basic nitrogen-containing heteroaromatic rings. The heteroaromatic group may independently be a five membered, a six membered, or a bulky basic nitrogen-containing heteroaromatic ring. The heteroaromatic ring may be substituted or unsubstituted. The substituent on the heteroaromatic ring may be C1-C6 saturated alkyl group, C3-C6 cycloalkyl group, —F, or $CF_3$.

For the scaffold represented by general formula (IV), the curcumin analog compounds are characterized by a seven carbon linker with acetone as the monoketone moiety and two terminal, basic nitrogen-containing heteroaromatic rings. The heteroaromatic group may independently be a five membered, a six membered, or a bulky basic nitrogen-containing heteroaromatic ring. The heteroaromatic ring may be substituted or unsubstituted. The substituent on the heteroaromatic ring may be C1-C6 saturated alkyl group, C3-C6 cycloalkyl group, —F, or $CF_3$.

The general formulas (I)-(IV) represent four synthetic scaffolds that were identified as possible improvements on the naturally occurring curcumin compound because each of these four scaffolds simultaneously possesses (1) a central monoketone linker instead of the β-diketone linker in the natural curcumin, and (2) two identical or different terminal basic heteroaromatic rings rather than the substituted phenyl ring in the natural curcumin. There are several rationalities for the synthetic scaffolds to have improved anti-cancer efficacy compared to naturally occurring curcumin.

The basicity of the nitrogen atom in the aromatic heterocycles will result in the target analogs being partially or completely protonated when they first encounter the acidic environment of the stomach to give the cationic form. Ionization will increase the compound's bioavailability due to its high water solubility and will enable the target analogs to reach the intestines. When the target analogs reach the basic conditions of the human intestines, the target analogs will be deprotonated, and the uncharged form will predominate. The uncharged, neutral analogs then can cross the intestine membrane at an appreciable rate into the bloodstream, leading to better bioavailability. The lack of several of curcumin's structural features which impose metabolic liabilities, also improves the bioavailability of target analogs due to decreased in vivo metabolism, making the curcumin analog compounds more stable. Specifically, the two phenolic hydroxyls in curcumin are susceptible to phase II metabolism, and the two methoxy substituents are susceptible to oxidative demethylation (Kania, 2009).

Heteroaromatic rings have been shown to be good bioisoteres of phenyl (Silverman, 2004), leading to better anticancer activity of the target analogs. Replacement of the metabolically unstable β-diketone linker with a monoketone linker will slow in vivo metabolism, making the curcumin analog compounds more stable.

C. SIDE GROUPS

The side groups for any curcumin analog scaffold depicted as one of general formulas (I)-(IV) independently may be a five membered heteroaromatic ring, a six membered heteroaromatic ring, or a bulky basic nitrogen-containing heteroaromatic ring. The heteroaromatic ring may be substituted or unsubstituted. The substituent on the heteroaromatic ring may be C1-C6 saturated alkyl group, C3-C6 cycloalkyl group, —F, or $CF_3$.

The side groups for any curcumin analog scaffold depicted as one of general formulas (I)-(IV) may be a five membered heteroaromatic ring as shown in Table 1. The label under each side group shown in Table 1 identifies the side group for correlation with specific compounds listed in Table 4.
TABLE 1
Structures of five-membered basic heteroaromatic rings
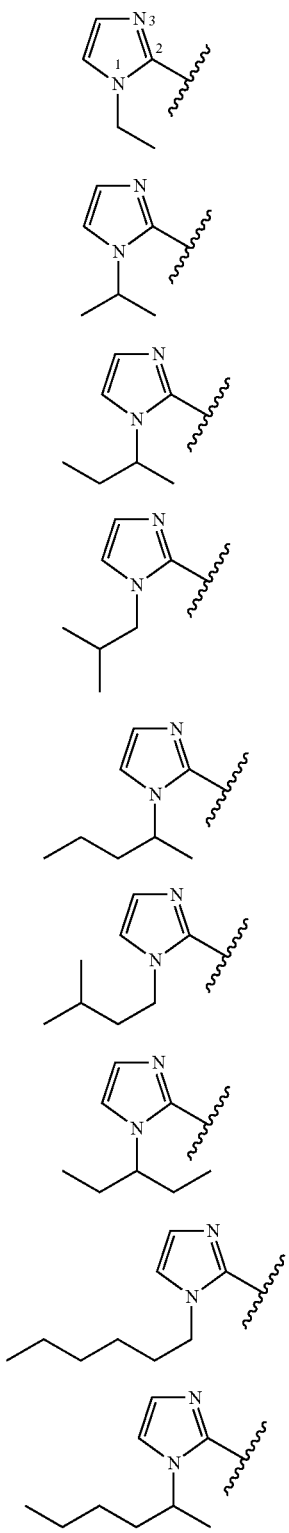
TABLE 1-continued
Structures of five-membered basic heteroaromatic rings
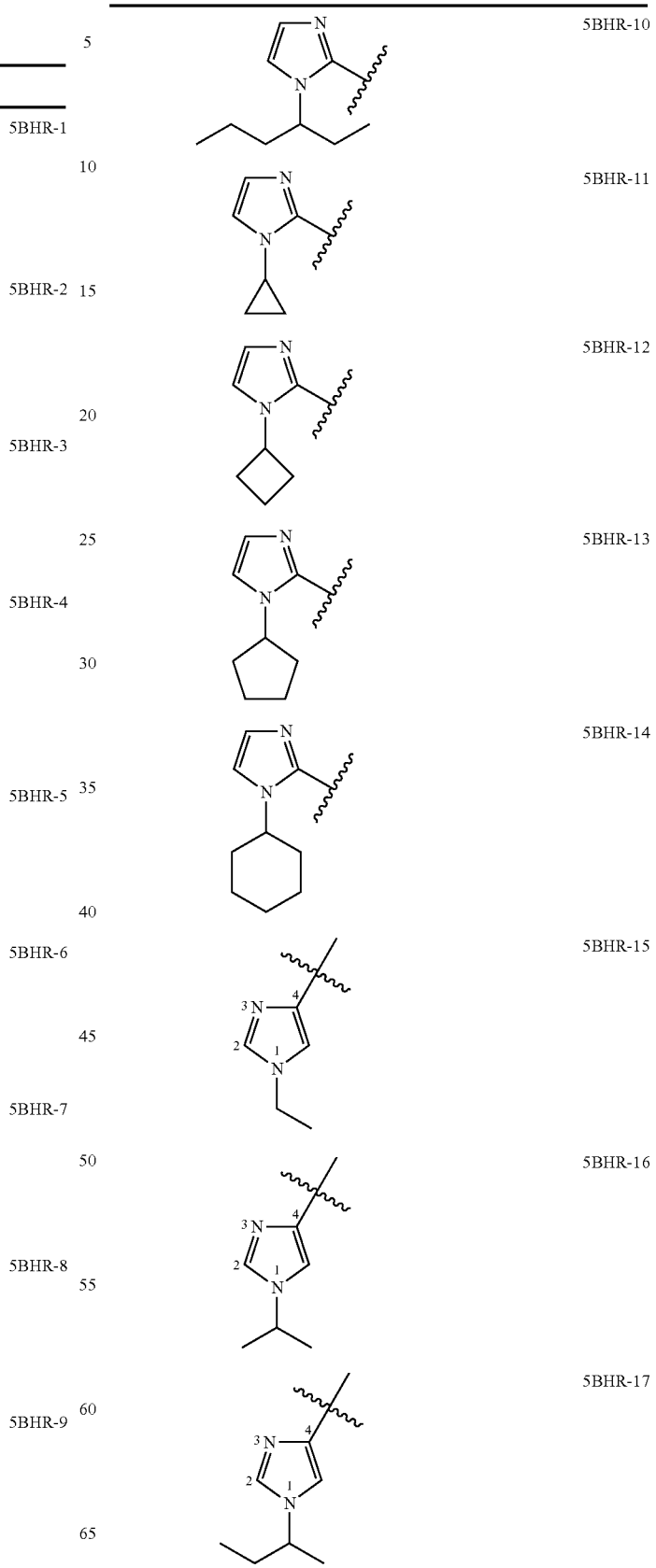

TABLE 1-continued
Structures of five-membered basic heteroaromatic rings
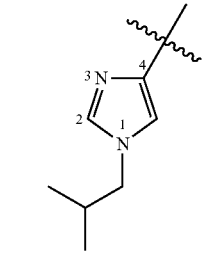 [SMILES: *c1cn(CC(C)C)cn1]
5BHR-18
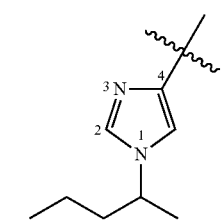 [SMILES: *c1cn(C(C)CCC)cn1]
5BHR-19
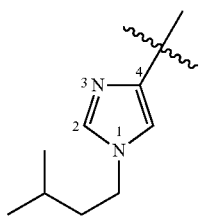 [SMILES: *c1cn(CCC(C)C)cn1]
5BHR-20
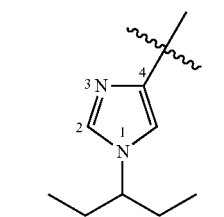 [SMILES: *c1cn(C(CC)CC)cn1]
5BHR-21
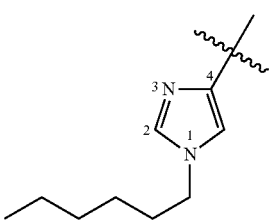 [SMILES: *c1cn(CCCCCC)cn1]
5BHR-22
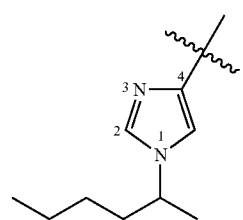 [SMILES: *c1cn(C(C)CCCC)cn1]
5BHR-23
TABLE 1-continued
Structures of five-membered basic heteroaromatic rings
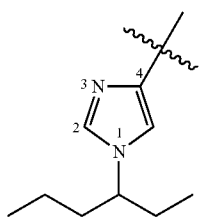 [SMILES: *c1cn(C(CC)CCC)cn1]
5BHR-24
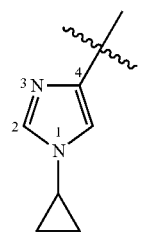 [SMILES: *c1cn(C2CC2)cn1]
5BHR-25
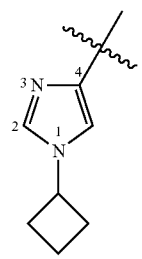 [SMILES: *c1cn(C2CCC2)cn1]
5BHR-26
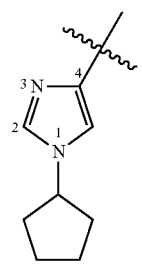 [SMILES: *c1cn(C2CCCC2)cn1]
5BHR-27
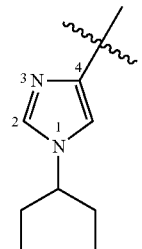
5BHR-28
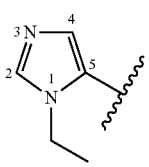
5BHR-29

TABLE 1-continued
Structures of five-membered basic heteroaromatic rings
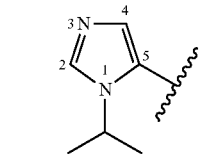 5BHR-30
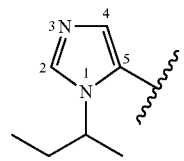 5BHR-31
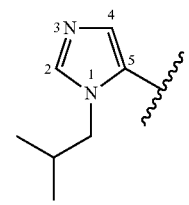 [SMILES: *c1cncn1CC(C)C] 5BHR-32
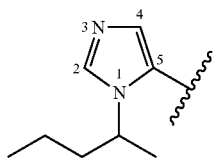 5BHR-33
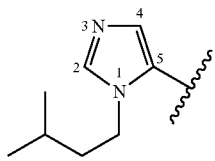 [SMILES: *c1cncn1CCC(C)C] 5BHR-34
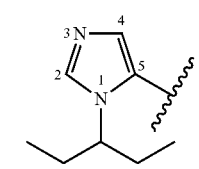 5BHR-35
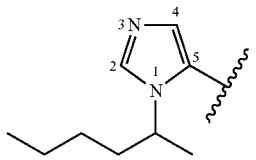 5BHR-36
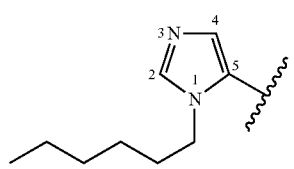 5BHR-37
TABLE 1-continued
Structures of five-membered basic heteroaromatic rings
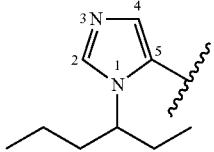 5BHR-38
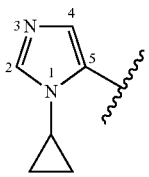 5BHR-39
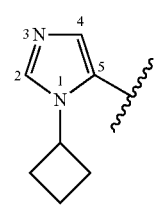 5BHR-40
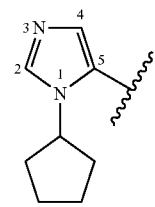 5BHR-41
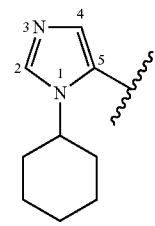 [SMILES: *c1cncn1C1CCCCC1] 5BHR-42
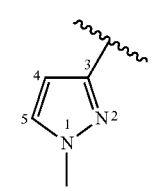 5BHR-43
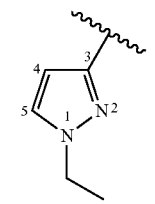 [SMILES: *c1ccn(CC)n1] 5BHR-44

TABLE 1-continued
Structures of five-membered basic heteroaromatic rings
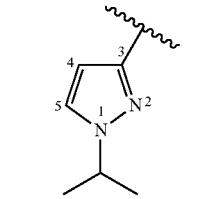 [SMILES: *c1ccn(C(C)C)n1] 5BHR-45
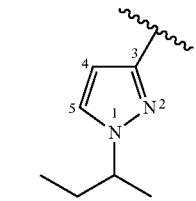 [SMILES: *c1ccn(C(C)CC)n1] 5BHR-46
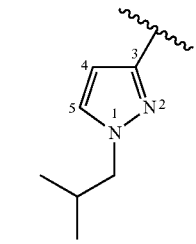 [SMILES: *c1ccn(CC(C)C)n1] 5BHR-47
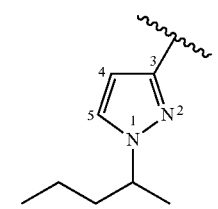 [SMILES: *c1ccn(C(C)CCC)n1] 5BHR-48
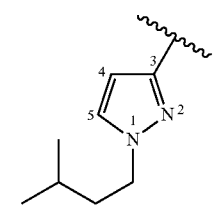 [SMILES: *c1ccn(CCC(C)C)n1] 5BHR-49
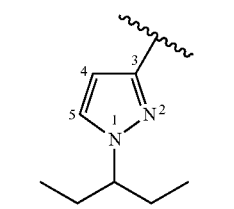 [SMILES: *c1ccn(C(CC)CC)n1] 5BHR-50
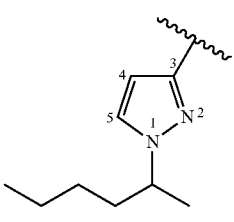 [SMILES: *c1ccn(C(C)CCCC)n1] 5BHR-51
TABLE 1-continued
Structures of five-membered basic heteroaromatic rings
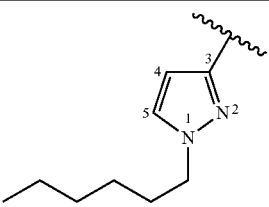 5BHR-52
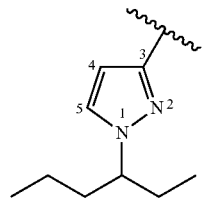 [SMILES: *c1ccn(C(CC)CCC)n1] 5BHR-53
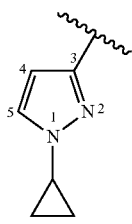 [SMILES: *c1ccn(C2CC2)n1] 5BHR-54
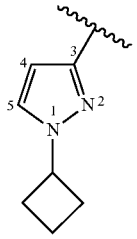 [SMILES: *c1ccn(C2CCC2)n1] 5BHR-55
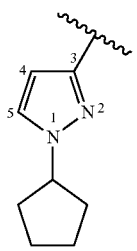 [SMILES: *c1ccn(C2CCCC2)n1] 5BHR-56
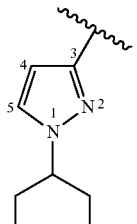 5BHR-57
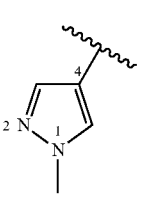 [SMILES: *c1cnn(C)c1] 5BHR-58

TABLE 1-continued
Structures of five-membered basic heteroaromatic rings
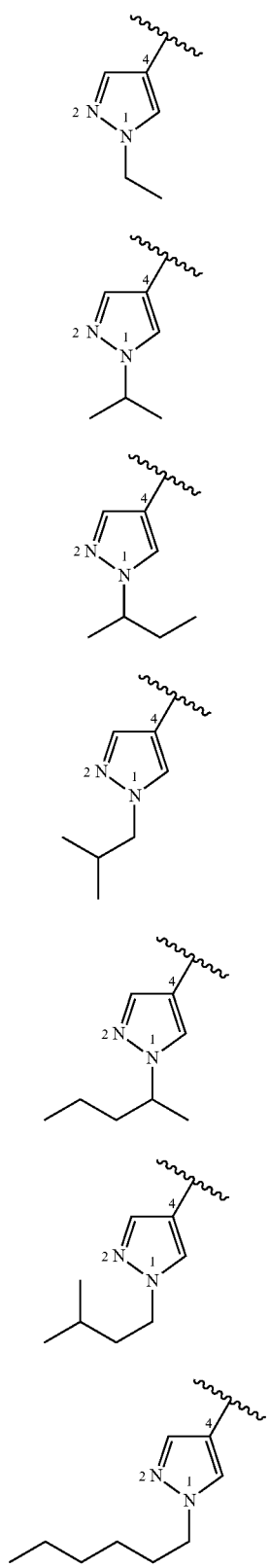
5BHR-59
5BHR-60
5BHR-61
5BHR-62
5BHR-63
5BHR-64
5BHR-65
TABLE 1-continued
Structures of five-membered basic heteroaromatic rings
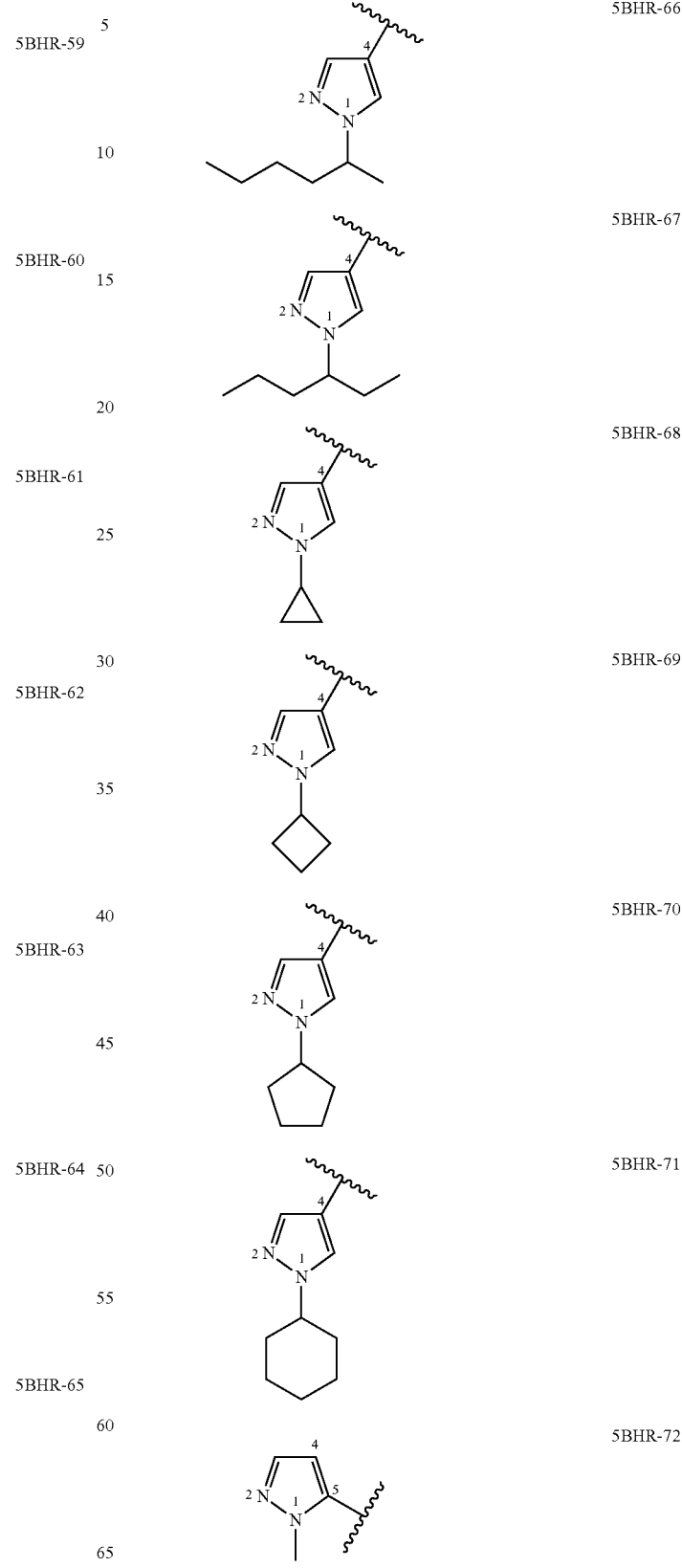
5BHR-66
5BHR-67
5BHR-68
5BHR-69
5BHR-70
5BHR-71
5BHR-72

TABLE 1-continued
Structures of five-membered basic heteroaromatic rings
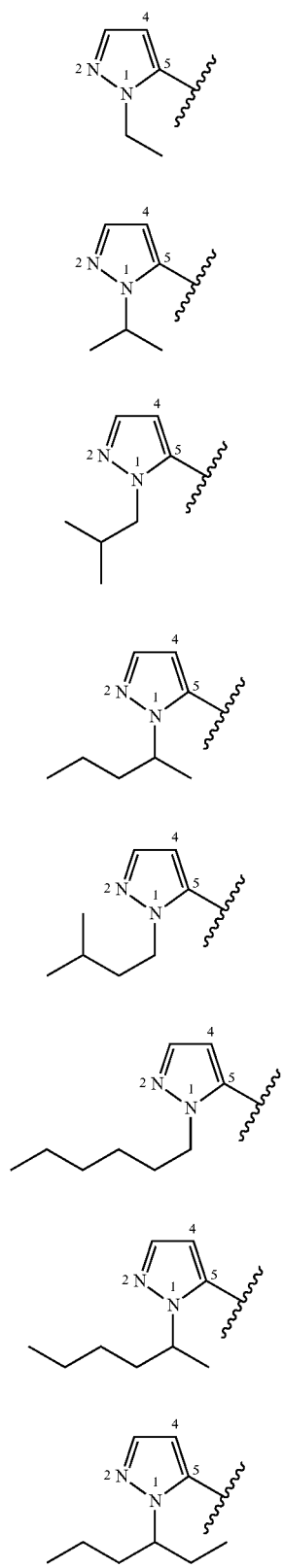
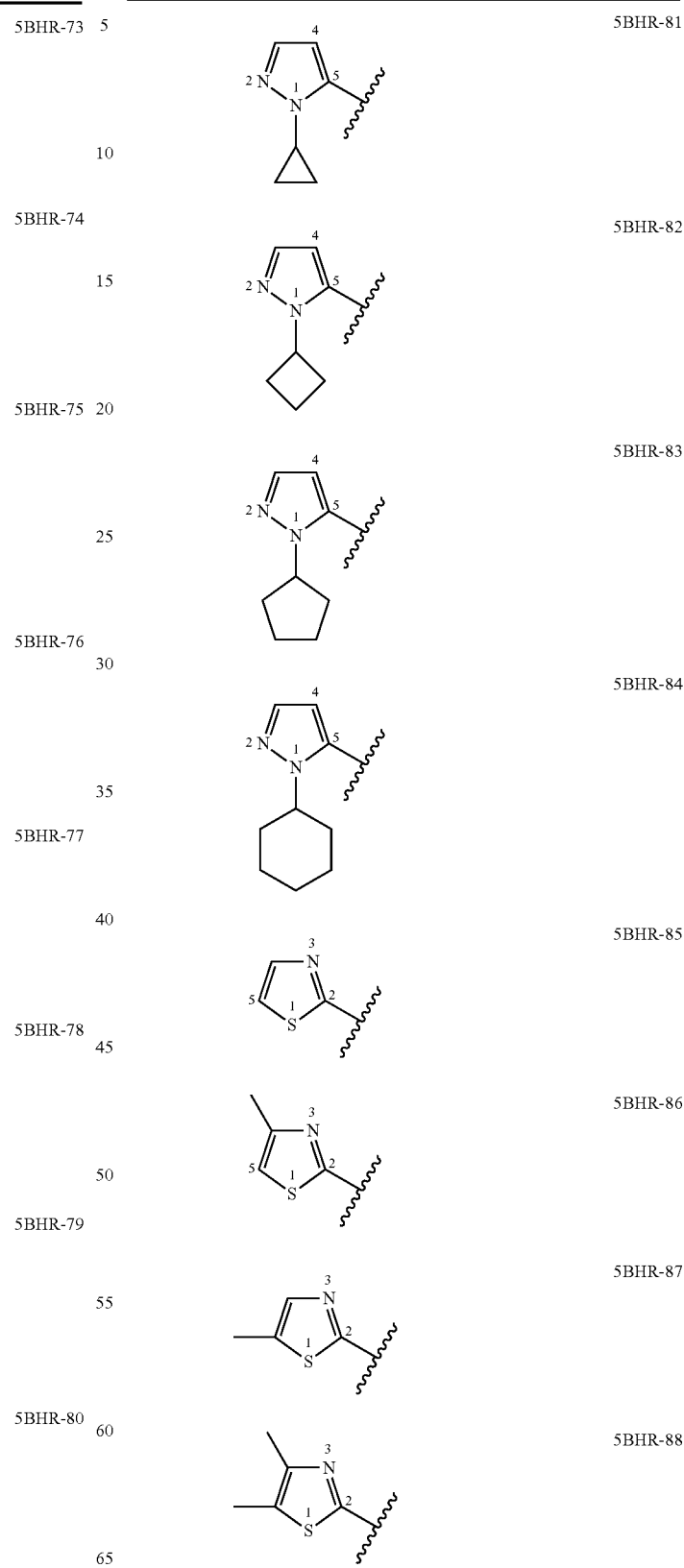

TABLE 1-continued
Structures of five-membered basic heteroaromatic rings
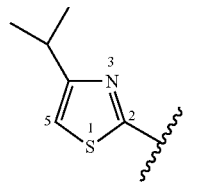 5BHR-89
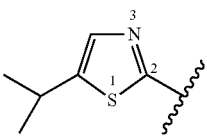 5BHR-90
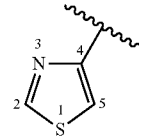 5BHR-91
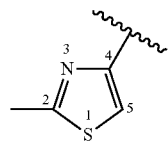 [SMILES: *c1csc(C)n1] 5BHR-92
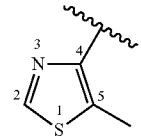 [SMILES: *c1ncsc1C] 5BHR-93
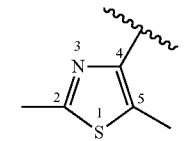 5BHR-94
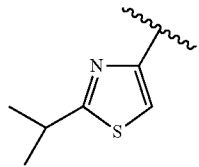 [SMILES: *c1csc(C(C)C)n1] 5BHR-95
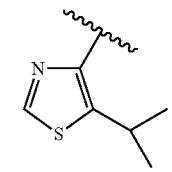 [SMILES: *c1ncsc1C(C)C] 5BHR-96
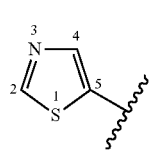 5BHR-97
TABLE 1-continued
Structures of five-membered basic heteroaromatic rings
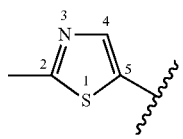 5BHR-98
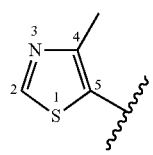 5BHR-99
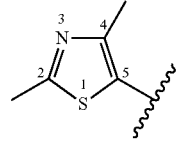 [SMILES: *c1sc(C)nc1C] 5BHR-100
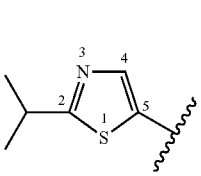 5BHR-101
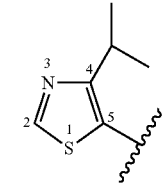 [SMILES: *c1scnc1C(C)C] 5BHR-102
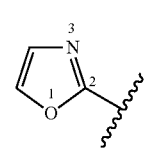 5BHR-103
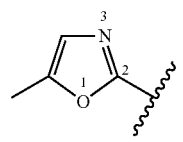 5BHR-104
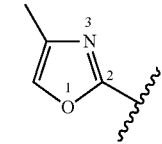 5BHR-105
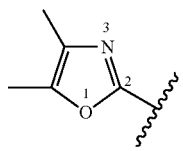 [SMILES: *c1nc(C)c(C)o1] 5BHR-106

TABLE 1-continued
Structures of five-membered basic heteroaromatic rings
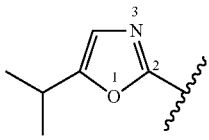 5BHR-107
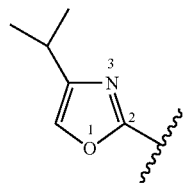 [SMILES: *c1nc(C(C)C)co1] 5BHR-108
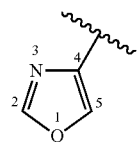 [SMILES: *c1cocn1] 5BHR-109
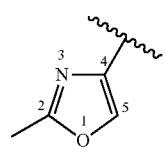 [SMILES: *c1coc(C)n1] 5BHR-110
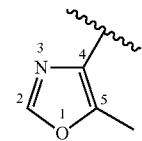 [SMILES: *c1ncoc1C] 5BHR-111
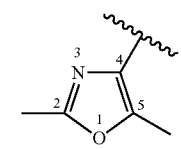 5BHR-112
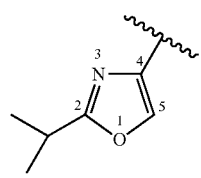 [SMILES: *c1coc(C(C)C)n1] 5BHR-113
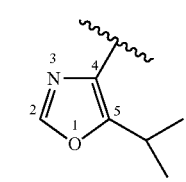 [SMILES: *c1ncoc1C(C)C] 5BHR-114
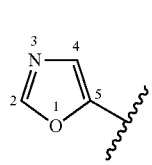 5BHR-115
TABLE 1-continued
Structures of five-membered basic heteroaromatic rings
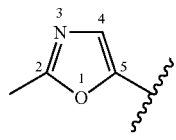 5BHR-116
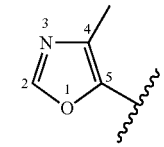 5BHR-117
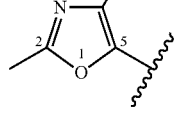 5BHR-118
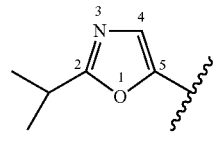 5BHR-119
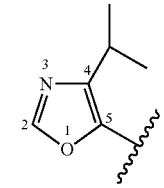 [SMILES: *c1ocnc1C(C)C] 5BHR-120
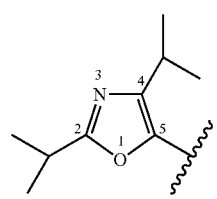 [SMILES: *c1oc(C(C)C)nc1C(C)C] 5BHR-121
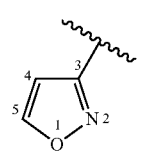 5BHR-122
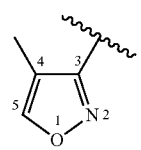 5BHR-123
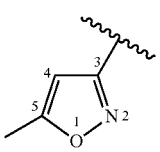 [SMILES: *c1cc(C)on1] 5BHR-124

TABLE 1-continued

Structures of five-membered basic heteroaromatic rings

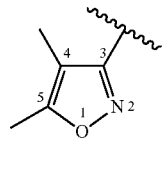 [SMILES: *c1noc(C)c1C] 5BHR-125

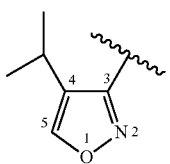 [SMILES: *c1nocc1C(C)C] 5BHR-126

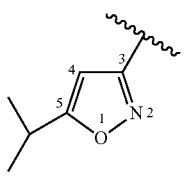 [SMILES: *c1cc(C(C)C)on1] 5BHR-127

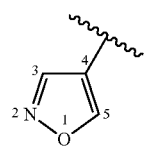 5BHR-128

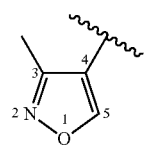 5BHR-129

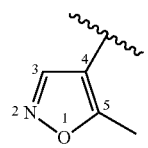 [SMILES: *c1cnoc1C] 5BHR-130

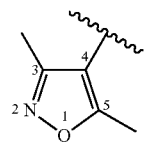 5BHR-131

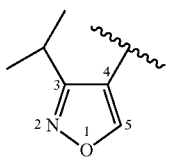 [SMILES: *c1conc1C(C)C] 5BHR-132

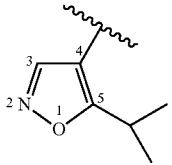 [SMILES: *c1cnoc1C(C)C] 5BHR-133

TABLE 1-continued

Structures of five-membered basic heteroaromatic rings

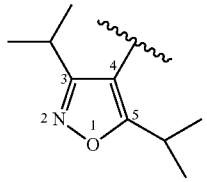 [SMILES: *c1c(C(C)C)noc1C(C)C] 5BHR-134

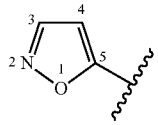 5BHR-135

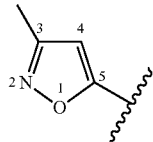 [SMILES: *c1cc(C)no1] 5BHR-136

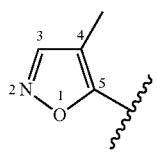 [SMILES: *c1oncc1C] 5BHR-137

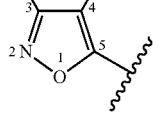 5BHR-138

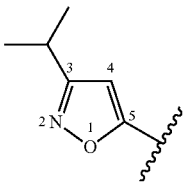 [SMILES: *c1cc(C(C)C)no1] 5BHR-139

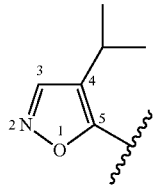 5BHR-140

The side group structures in Table 1 can be characterized as containing a five membered ring comprised of a continuously overlapping p orbital and two heteroatoms such as oxygen, sulfur, or nitrogen. One of the two heteroatoms must be basic nitrogen. The heteroaromatic ring may be substituted or unsubstituted. The substituent on the heteroaromatic ring may be C1-C6 saturated alkyl group, C3-C6 cycloalkyl group, —F, or $CF_3$.

These five membered heteroaromatic ring side groups attached to any of the curcumin analog scaffolds depicted as general formulas (I)-(IV) should increase efficacy in cancer treatment due to three reasons. First, the basicity of the nitrogen atom in the five membered aromatic heterocycles will cause the target analogs to be partially or completely protonated when they encounter the acidic environment of the stomach, resulting in the cationic form. The ionization will increase the compound's bioavailability due to its high water solubility and will enable the target analogs to reach the intestine. When the target analogs having the five membered heteroaromatic ring side groups reach the basic conditions of the intestines, they will be deprotonated, and the uncharged form will predominate. The target analogs then can cross the intestine membrane at an appreciable rate into the bloodstream, resulting in improved bioavailability.

Secondly, these five membered heteroaromatic ring side groups attached to any of the curcumin analog scaffolds depicted as general formulas (I)-(IV) lack curcumin's two phenolic hydroxyls and two methoxy substituents, thereby improving the bioavailability of target analogs due to decreased in vivo metabolism, making the analog structures more stable (Kania, 2009). Specifically, the two phenolic hydroxyls in curcumin are susceptible to phase II metabolism; the two methoxy substituents are liabilities for oxidative demethylation. Thirdly, the five membered heteroaromatic rings—which are electron rich aromatic rings—have been shown to be good bioisoteres of a phenyl (Silverman, 2004), therefore retaining or enhancing anticancer potency.

The side groups for any scaffold depicted as one of general formulas (I)-(IV) may be a six membered heteroaromatic ring as shown in Table 2. The label under each side group shown in Table 2 identifies the side group for correlation with specific compounds listed in Table 4.

TABLE 2

Structures of six-membered basic heteroaromatic rings

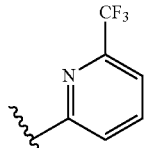
6BHR-1

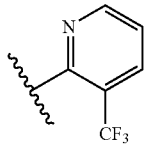
6BHR-2

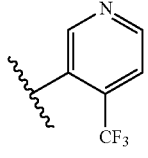
6BHR-3

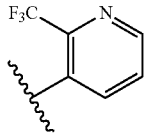 [SMILES: *c1cccnc1C(F)(F)F]
6BHR-4

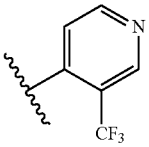
6BHR-5

TABLE 2-continued

Structures of six-membered basic heteroaromatic rings

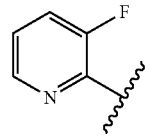 [SMILES: *c1ncccc1F]
6BHR-6

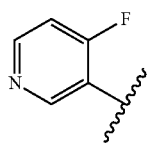
6BHR-7

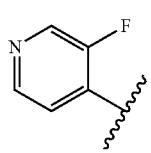
6BHR-8

The side group structures in Table 2 can be characterized as containing a six membered ring comprised of continuously overlapping p orbital and of one basic nitrogen. The six membered heteroaromatic ring may be unsubstituted or substituted —F, or $CF_3$. These six membered heteroaromatic ring side groups attached to any of the scaffolds depicted as general formulas (I)-(IV) should increase efficacy in cancer treatment because of three reasons.

Firstly, the basicity of the nitrogen atom in the six membered heteroaromatic ring causes the target analogs to be partially or completely protonated when they encounter the acidic stomach environment, resulting in the cationic form. The ionization of the target analog increases the compound's bioavailability due to its high water solubility. When the target analogs reach the basic conditions of the intestines, they will be deprotonated, and the uncharged form will predominate. They can then cross the intestine membrane at an appreciable rate into the bloodstream, resulting in better bioavailability.

Secondly, these six membered heteroaromatic ring side groups attached to any of the curcumin analog scaffolds depicted as general formulas (I)-(IV) lack curcumin's two phenolic hydroxyls and two methoxy substituents, thereby improving the bioavailability of target analogs due to decreased in vivo metabolism, making the analog structures more stable (Kania, 2009). Specifically, the two phenolic hydroxyls in curcumin are susceptible to phase II metabolism; the two methoxy substituents are liabilities for oxidative demethylation. Thirdly, six membered heteroaromatic rings are electron deficient, which possess enforced interactions with electron rich protein targets, leading to higher anti-cancer potency.

The side groups for any scaffold depicted as one of general formulas (I)-(IV) may be a bulky basic nitrogen-containing heteroaromatic ring as shown in Table 3. The label under each side group shown in Table 3 identifies the side group for correlation with specific compounds listed in Table 4.

TABLE 3
Structures of bulky basic heteroaromatic rings
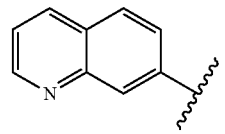 [SMILES: *c1ccc2cccnc2c1]
BBHR-1001
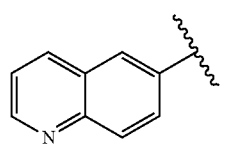 [SMILES: *c1ccc2ncccc2c1]
BBHR-1002
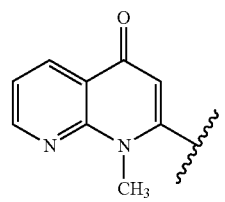 [SMILES: *c1cc(=O)c2cccnc2n1C]
BBHR-1003
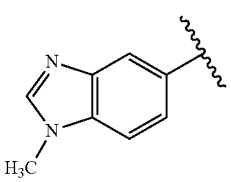 [SMILES: *c1ccc2c(c1)ncn2C]
BBHR-1004
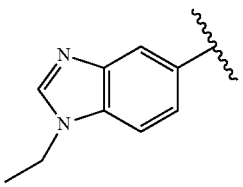 [SMILES: *c1ccc2c(c1)ncn2CC]
BBHR-1005
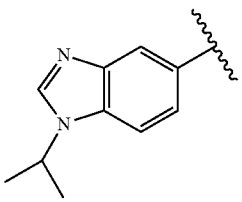 [SMILES: *c1ccc2c(c1)ncn2C(C)C]
BBHR-1006
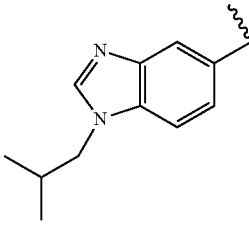
BBHR-1007
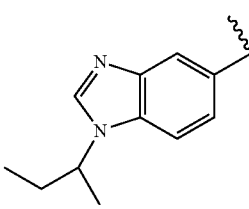
BBHR-1008
TABLE 3-continued
Structures of bulky basic heteroaromatic rings
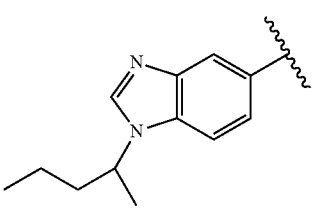 [SMILES: *c1ccc2c(c1)ncn2C(C)CCC]
BBHR-1009
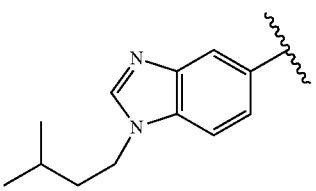 [SMILES: *c1ccc2c(c1)ncn2CCC(C)C]
BBHR-1010
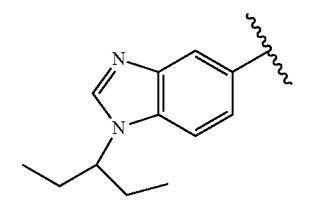 [SMILES: *c1ccc2c(c1)ncn2C(CC)CC]
BBHR-1011
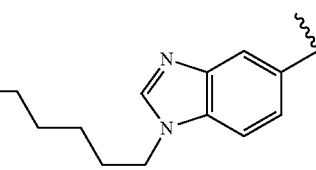
BBHR-1012
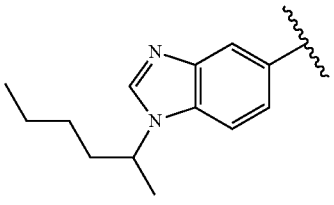 [SMILES: *c1ccc2c(c1)ncn2C(C)CCCC]
BBHR-1013
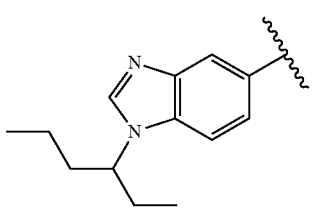 [SMILES: *c1ccc2c(c1)ncn2C(CC)CCC]
BBHR-1014

TABLE 3-continued
Structures of bulky basic heteroaromatic rings
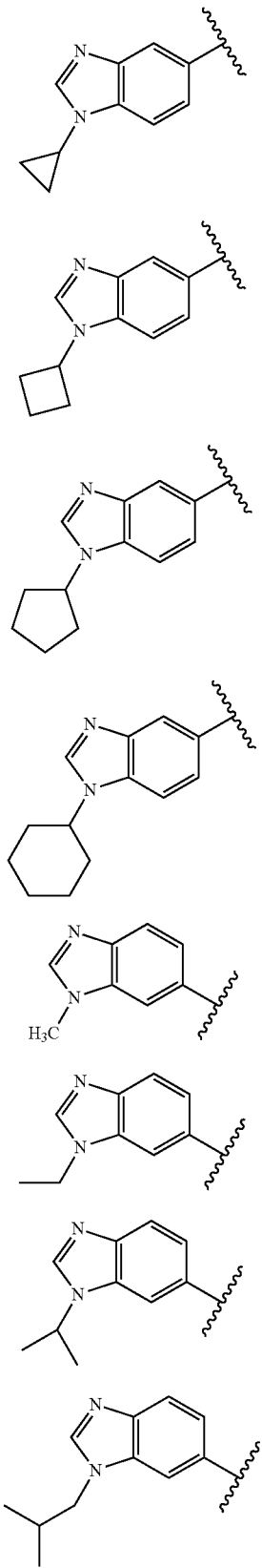
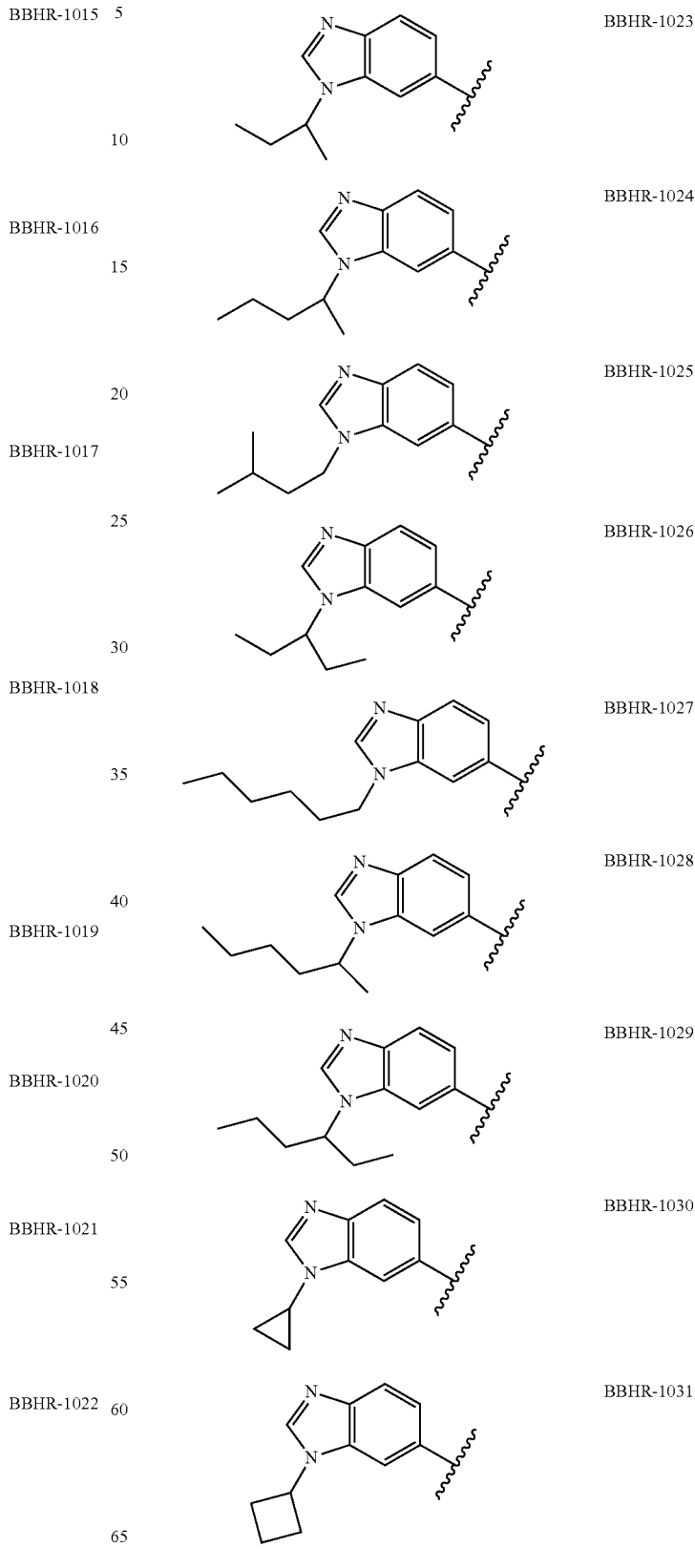

TABLE 3-continued
Structures of bulky basic heteroaromatic rings
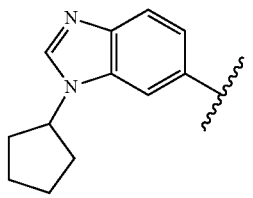 [SMILES: *c1ccc2ncn(C3CCCC3)c2c1] BBHR-1032
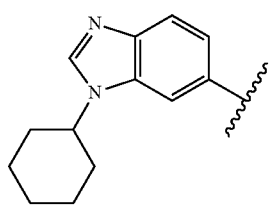 [SMILES: *c1ccc2ncn(C3CCCCC3)c2c1] BBHR-1033
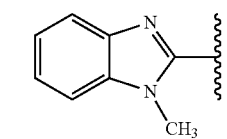 BBHR-1034
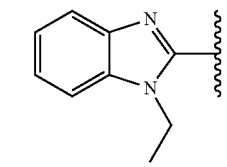 [SMILES: *c1nc2ccccc2n1CC] BBHR-1035
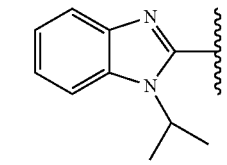 [SMILES: *c1nc2ccccc2n1C(C)C] BBHR-1036
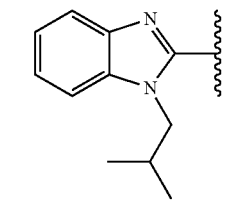 [SMILES: *c1nc2ccccc2n1CC(C)C] BBHR-1037
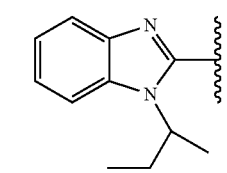 [SMILES: *c1nc2ccccc2n1C(C)CC] BBHR-1038
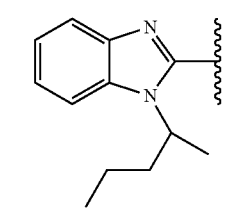 [SMILES: *c1nc2ccccc2n1C(C)CCC] BBHR-1039
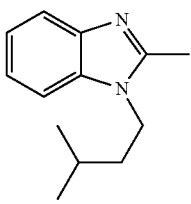 BBHR-1040
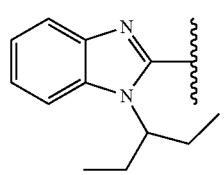 [SMILES: *c1nc2ccccc2n1C(CC)CC] BBHR-1041
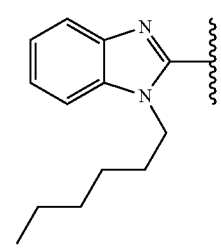 [SMILES: *c1nc2ccccc2n1CCCCCC] BBHR-1042
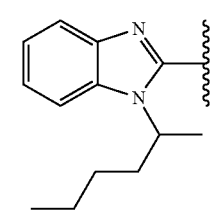 [SMILES: *c1nc2ccccc2n1C(C)CCCC] BBHR-1043
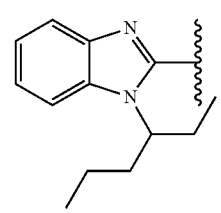 [SMILES: *c1nc2ccccc2n1C(CC)CCC] BBHR-1044
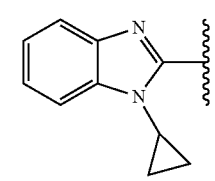 [SMILES: *c1nc2ccccc2n1C1CC1] BBHR-1045
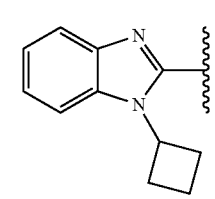 [SMILES: *c1nc2ccccc2n1C1CCC1] BBHR-1046

TABLE 3-continued

Structures of bulky basic heteroaromatic rings

| Structure | ID |
|---|---|
| (benzimidazole with N-cyclopentyl) | BBHR-1047 |
| (benzimidazole with N-cyclohexyl) | BBHR-1048 |
| (benzoxazole) | BBHR-1049 |
| (2-methylbenzoxazole) | BBHR-1050 |
| (2-isopropylbenzoxazole) | BBHR-1051 |
| (benzoxazole isomer) | BBHR-1052 |
| (2-methylbenzoxazole isomer) | BBHR-1053 |
| (2-isopropylbenzoxazole isomer) | BBHR-1054 |
| (benzothiazole) | BBHR-1055 |
| (2-methylbenzothiazole) | BBHR-1056 |
| (2-isopropylbenzothiazole) | BBHR-1057 |
| (benzothiazole isomer) | BBHR-1058 |
| (2-methylbenzothiazole isomer) | BBHR-1059 |
| (2-isopropylbenzothiazole isomer) | BBHR-1060 |
| (2-benzoxazolyl) | BBHR-1061 |
| (2-benzothiazolyl) | BBHR-1062 |

The side structures shown in Table 3 can be characterized by a bulky basic heteroaromatic ring that contains a five membered basic nitrogen containing heteroaromatic ring fused with a benzene. The bulky heteroaromatic ring may be substituted or unsubstituted. The substituent on the bulky heteroaromatic ring may be C1-C6 saturated alkyl group, C3-C6 cycloalkyl group, —F, or $CF_3$. These bulky basic nitrogen-containing heteroaromatic ring side groups attached to any of the scaffolds depicted as general formulas (I)-(IV) should increase efficacy in cancer treatment due to three reasons.

Firstly, the basicity of the nitrogen atom in the bulky aromatic rings will lead to ionized compounds at physiological pH and improved water solubility. Secondly, these bulky heteroaromatic ring side groups attached to any of the curcumin analog scaffolds depicted as general formulas (I)-(IV) lack curcumin's two phenolic hydroxyls and two methoxy substituents, thereby improving the bioavailability of target analogs due to decreased in vivo metabolism, making the analog structures more stable. Specifically, the two phenolic hydroxyls in curcumin are susceptible to phase II metabolism; the two methoxy substituents are liabilities for oxidative demethylation (Kania, 2009). Thirdly, bulky heteroaromatic rings can enforce the interactions between the curcumin analog and its binding targets by increased pi-pi interaction and hydrogen bonding. Nitrogen is a good hydrogen bonding acceptor, which can generate a hydrogen bonding between the analog and an appropriate receptor, eventually enhancing its anticancer potency.

Table 4 shows the curcumin analog compounds that were synthesized and tested for biological effects. Table 4 shows the general scaffold and the side groups for each compound.

TABLE 4

Synthesized curcumin analogs

| Compound No. | General Formula | BHR₁ and BHR₂ (Refer to Tables 1-3) |
|---|---|---|
| 1 | (I) | 5BHR-2 |
| 2 | (I) | 5BHR-3 |
| 3 | (I) | 5BHR-58 |
| 4 | (I) | 5BHR-72 |
| 5 | (I) | 5BHR-85 |
| 6 | (I) | 5BHR-91 |
| 7 | (I) | 5BHR-110 |
| 8 | (I) | 5BHR-124 |
| 9 | (I) | 5BHR-136 |
| 10 | (II) | 5BHR-2 |
| 11 | (II) | 5BHR-3 |
| 12 | (II) | 5BHR-4 |
| 13 | (II) | 5BHR-58 |
| 14 | (II) | 5BHR-72 |
| 15 | (II) | 5BHR-85 |
| 16 | (II) | 5BHR-91 |
| 17 | (II) | 5BHR-110 |
| 18 | (II) | 5BHR-124 |
| 19 | (II) | 5BHR-136 |
| 20 | (III) | 5BHR-2 |
| 21 | (III) | 5BHR-3 |
| 22 | (III) | 5BHR-4 |
| 23 | (III) | 5BHR-72 |
| 24 | (III) | 5BHR-85 |
| 25 | (III) | 5BHR-91 |
| 26 | (III) | 5BHR-110 |
| 27 | (III) | 5BHR-124 |
| 28 | (III) | 5BHR-136 |
| 29 | (III) | 5BHR-97 |
| 30 | (III) | 5BHR-131 |
| 31 | (III) | 5BHR-86 |
| 32 | (III) | 5BHR-7 |
| 33 | (III) | 5BHR-6 |
| 34 | (III) | 5BHR-5 |
| 35 | (III) | 5BHR-8 |
| 36 | (III) | 6BHR-8 |
| 37 | (III) | 5BHR-109 |
| 38 | (III) | 5BHR-58 |
| 39 | (III) | BBHR-1034 |
| 40 | (III) | BBHR-1036 |
| 41 | (III) | BBHR-1037 |
| 42 | (III) | BBHR-1038 |
| 43 | (III) | BBHR-1039 |
| 44 | (III) | BBHR-1040 |
| 45 | (III) | BBHR-1041 |
| 46 | (III) | BBHR-1027 |

D. SYNTHESIS OF CHEMICAL SCAFFOLDS DEPICTED AS GENERAL FORMULAS (I)-(IV)

As shown in FIG. 1, the curcumin analogs having a scaffold represented by general formula (I) can be synthesized by double aldol condensation of two equivalents of the appropriate basic heteroarylformaldehyde with N-methylpiperidone following the procedure reported in the literature (Yadav et al., 2010). Most of the basic heteroarylformaldehydes are commercially available. The reaction starts with enolization of N-methylpiperidone in the presence of sodium methoxide as base. The nucleophilic addition of the enolate intermediate to the carbonyl group of heteroarylformaldehyde generates β-hydroxyl ketone, which can be converted to α,β-unsaturated ketone after elimination of one molecular of water. The nucleophilic addition of the subsequent enolate, generated from deprotonation of the α,β-unsaturated ketone using sodium methoxide as base, to the carbonyl group of the second molecule aldehyde, followed by elimination of the second molecular of water, generates the desired curcumin analogs having a scaffold represented by general formula (I).

Figure 2:
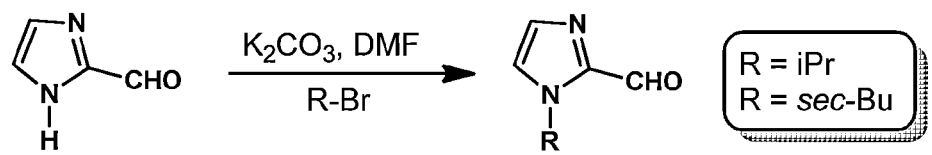
FIG. 2 shows a synthesis process to produce 1-alkyl-1H-imidazolde-2-carbaldehyde.

As shown in FIG. 2, 1-alkyl-1H-imidazole-2-carbaldehyde, general formula (I), side group 5BHR-2 to 5BHR-14, was prepared from 1H-imidazole-2-carbaldehyde using potassium carbonate as base according to the procedure described in the literature (Seto et al., 2005). Briefly, potassium carbonate serves as a base. Abstraction of acidic hydrogen from 1H-imidazole-2-carbaldehyde by this base yields a nucleophilic nitrogen anion. This nupleophile reacts with electrophilic alkyl halide to generate the desired 1-alkyl-1H-imidazole-2-carbaldehyde.

Figure 3:
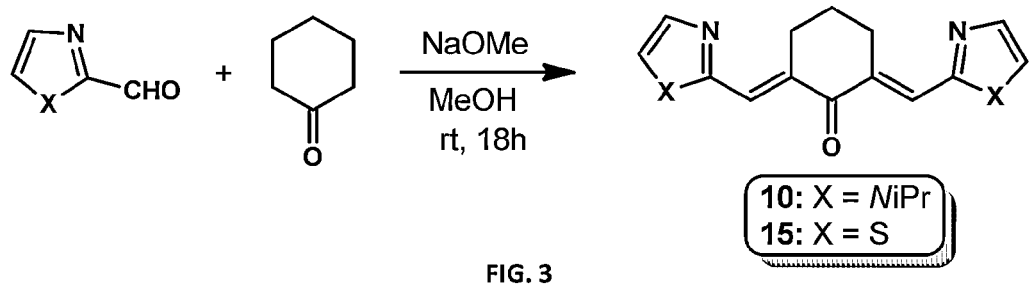
FIG. 3 shows a synthesis process to produce curcumin analogs having a scaffold represented by general formula (II).

As shown in FIG. 3, the curcumin analogs having scaffolds represented by general formula (II) can be synthesized via double aldol condensation of two equivalents of the appropriate basic heteroarylformaldehyde with cyclohexanone following the procedure reported in the literature (Yadav, et al., 2010). Most of the basic heteroarylformaldehydes are commercially available. Specifically, sodium methoxide can remove the acidic α-hydrogen of cyclohexanone to produce an enolate. Nucleophilic addition of this enolate to the appropriate basic heteroarylformaldehyde, followed by protonation, can generate an intermediate—β-hydroxyl ketone. Dehydration of the β-hydroxyl ketone can form a α,β-unsaturated ketone. The acidic α-proton of the α,β-unsaturated ketone can be deprotonated by sodium methoxide to form another enolate. Nucleophilic addition of this enolate to the second molecular of basic heteroarylformaldehyde, followed by elimination of another molecular of water, can form the curcumin analogs having a scaffold represented by general formula (II).

Figure 4A:
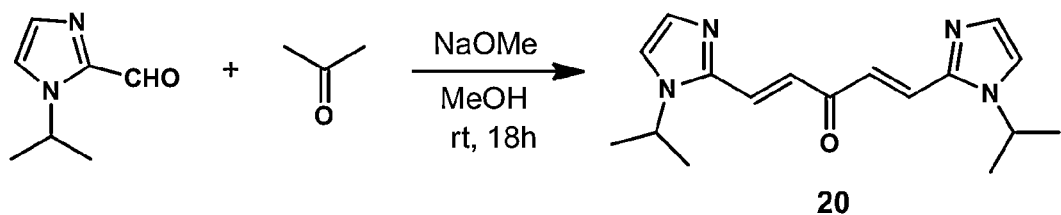
FIG. 4A shows a synthesis process to produce curcumin analogs having a scaffold represented by general formula (III), in which sodium methoxide serves as a base to abstract the acidic α-hydrogen of acetone to generate an enolate.
Figure 4B:
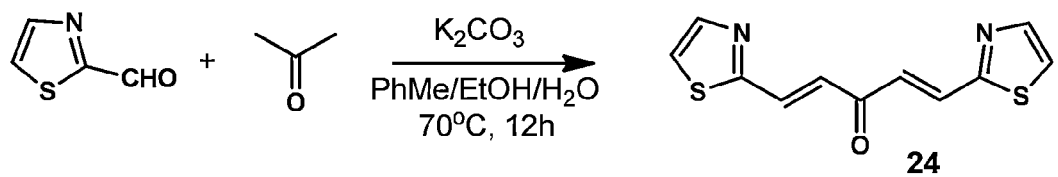
FIG. 4B shows a synthesis process to produce curcumin analogs having a scaffold represented by general formula (III) in which potassium carbonate serves as base to abstract the acidic α-hydrogen of acetone to generate an enolate.
Figure 5:
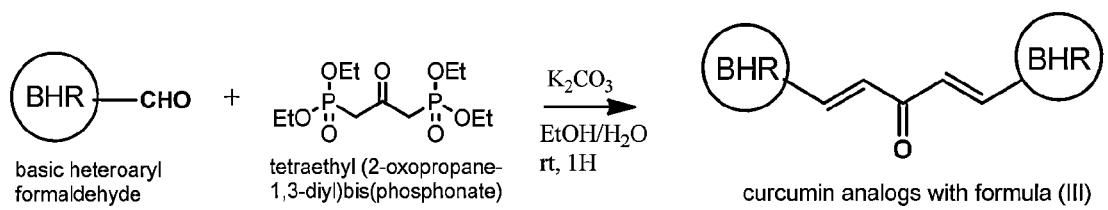
FIG. 5 shows the Horner-Wadsworth-Emmons reaction of 1,3-bis(diethylphosphonato)acetone with appropriate heteroarylformaldehydes to produce curcumin analogs having a scaffold represented by general formula (III).

As shown in FIGS. 4A, 4B and 5, there are three different methods that can be used to synthesize the curcumin analogs having scaffolds represented by general formula (III). As shown in FIG. 4A, the imidazole analog, general formula (III) with side group 5BHR-2, can be synthesized from the respective heteroarylformaldehyde and acetone using the procedure reported in the literature (Yadav, et al., 2010). Here, sodium methoxide can serve as a base to abstract the acidic α-hydrogen of acetone to generate an enolate. Nucleophilic addition of this enolate to the carbonyl group of the appropriate heteroarylformaldehyde, followed by dehydration, can yield an α,β-unsaturated ketone. The acidic α-proton of the α,β-unsaturated ketone can be deprotonated by sodium methoxide to form another enolate. Nucleophilic addition of this enolate to the carbonyl group of the second molecular of basic heteroarylformaldehyde, followed by elimination of another molecular of water, can form the curcumin analogs having a scaffold represented by general formula (III).

However, most of the curcumin analogs having a scaffold represented by general formula (III) cannot be prepared with sufficiently high yield by this method. Most curcumin analogs were prepared using potassium carbonate as base, as shown in FIG. 4B, following the procedure reported by Long and co-workers (Cao et al., 2012). Nucleophilic addition of this enolate to the carbonyl group of the appropriate heteroarylformaldehyde, followed by dehydration, can yield an α,β-unsaturated ketone. The acidic α-proton of the α,β-unsaturated ketone can be deprotonated by potassium carbonate to form another enolate. Nucleophilic addition of this enolate to the carbonyl group of the second molecular of basic heteroarylformaldehyde, followed by elimination of another molecular of water, can form the curcumin analogs having a scaffold represented by general formula (III).

The curcumin analogs having a scaffold represented by general formula (III) also can be synthesized through the Horner-Wadsworth-Emmons reaction of 1,3-bis(diethylphosphonato)acetone with appropriate heteroarylformaldehydes, using the reaction sequence illustrated in FIG. 5. This procedure was used to synthesize more than forty curcumin analogs having scaffolds represented by the general formula (III) (Sehnal, 2009). As shown in FIG. 5, the starting material, 1,3-bis(diethylphosphonato) acetone (CAS#: 1475-91-8), was prepared from carbazic acid methyl ester, 1,3-dichloroacetone, and triethyl phosphite according to the procedure described in the literature (Corbel, 1985).

As shown in FIG. 5, the Horner-Wadsworth-Emmons reaction begins with the deprotonation of the 1,3-bis(diethylphosphonato)acetone to give the phosphonate carbanion. Nucleophilic addition of the carbanion onto the aldehyde generates α-hydroxyphosphonate as an intermediate. The final elimination of the α-hydroxyphosphonate yields (E)-diethyl(2-oxo-4-heteroaryl-but-3-en-1-yl)phosphonate, which can be transformed to the curcumin analogs having a scaffold represented by general formula (III) after a repeated Horner-Wadsworth-Emmons reaction.

Figure 6:
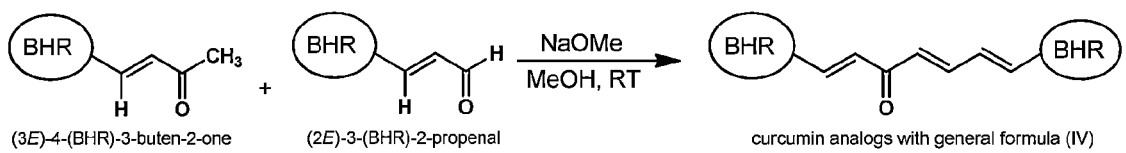
FIG. 6 shows a synthesis process for curcumin analogs having a scaffold represented by general formula (IV).

As shown in FIG. 6, the curcumin analogs having a scaffold represented by general formula (IV) can be synthesized by an aldol condensation reaction of (3E)-4-(BHR)-3-buten-2-one with (2E)-3-(BHR)-2-propenal in the presence of sodium methoxide. (3E)-4-(BHR)-3-buten-2-one can be readily synthesized by Wittig reaction of the appropriate basic heteroarylformaldehyde with 1-(triphenylphosphoranylidene)-2-propanone in toluene under refluxing (Le, et al., 2012). Similarly, (2E)-4-(BHR)-2-propenal can be easily prepared via Wittig reaction of the appropriate basic heteroarylformaldehyde with triphenylphosphoranylidene acetaldehyde at room temperature using DMF as solvent (van Loevezijn A., et al., 2011).

As shown in FIG. 6, the aldol condensation reaction starts with the deprotonation of the acidic hydrogen of (3E)-4-(BHR)-3-buten-2-one. The sodium methoxide functions as a base to grab the acidic hydrogen. The nucleophilic addition of the subsequent enolate onto the carbonyl group of (2E)-4-(BHR)-2-propenal yields a β-hydroxy ketone. The final dehydration leads to the formation of the curcumin analogs having a scaffold represented by general formula (IV). These reaction conditions can prevent the further Wittig reaction of the desired (2E)-4-(BHR)-2-propenal with triphenylphosphoranylidene acetaldedyde.

Figure 7:
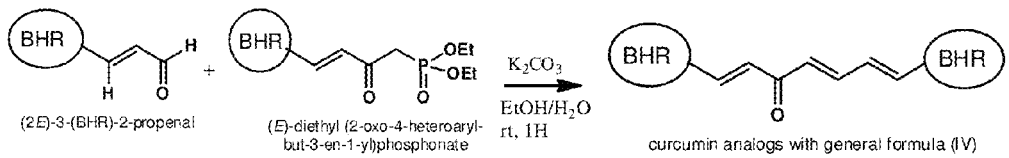
FIG. 7 shows an alternative synthesis process for curcumin analogs having a scaffold represented by general formula (IV).

Alternatively, as shown in FIG. 7, the curcumin analogs having a scaffold represented by general formula (IV) can be synthesized via the Horner-Wadsworth-Emmons reaction of (2E)-3-(BHR)-2-propenal with (E)-diethyl(2-oxo-4-heteroaryl-but-3-en-1-yl)phosphonate using potassium carbonate as base. The aldol condensation reaction, shown in FIG. 6, is used when the side groups are five membered heteroaromatic rings from 5BHR-2 to 5BHR-14 (see Table 1). The Horner-Wadsworth-Emmons reaction, shown in FIG. 7, is used when the target cannot be made through the procedure described in FIG. 6.

Figure 8:
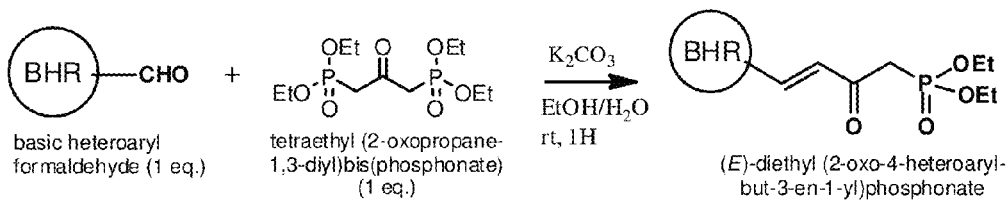
FIG. 8 shows a synthesis process producing (E)-diethyl (2-oxo-4-heteroarylbut-3-en-1-yl)phosphonate.

As shown in FIG. 8, the (E)-diethyl(2-oxo-4-heteroaryl-but-3-en-1-yl)phosphonate, general formula (IV), side groups 5BHR-2 to 5BHR-14 (see Table 1), and 6BHR-1 to 6BHR-8 (see Table 2), can be easily prepared by Horner-Wadsworth-Emmons reaction of one equivalent of 1,3-bis(diethylphosphonato)acetone with one equivalent of appropriate heteroarylformaldehydes. As shown in FIG. 8, the Horner-Wadsworth-Emmons reaction begins with deprotonation of 1,3-bis(diethylphosphonato)acetone to give the phosphonate carbanion. The potassium carbonate is the base to accept the acidic proton. Nucleophilic addition of the carbanion onto the aldehyde generates α-hydroxyphosphonate as an intermediate. The final elimination of a molecular of water from the α-hydroxyphosphonate generates (E)-diethyl(2-oxo-4-hetero aryl-but-3-en-1-yl)phosphonate.

Example 1

Synthesis of (2E,6E)-2,6-Bis((5-methylisoxazol-3-yl)methylene)cyclohexanone (General Formula (I), 5BHR-124 Side Group, Shown as Compound 8 in Table 4)

The solution of sodium methoxide in methanol (5.4 M, 0.14 mL, 0.75 mmol) was added to a solution of 5-methylisoxazole-3-carbaldehyde (166.5 mg, 1.5 mmol) and N-methylpiperidone (85 mg, 0.75 mmol) in methanol (10 mL). The mixture was stirred for 4 h-18 h and monitored with Thin Layer Chromatography (TLC). When the reaction was completed, saturated solution of ammonium chloride was added, and the subsequent mixture was extracted with dichloromethane. The organic layer was dried over anhydrous $MgSO_4$. The solvent was evaporated under vacuum to give a crude product, which was purified by preparative TLC (5% methanol in dichloromethane).

NMR spectra were obtained on a Bruker Fourier 300 spectrometer in CDC3, CD3OD, or DMSO-d6. The chemical shifts are given in d (ppm) referenced to the respective solvent peak, and coupling constants are reported in Hz. All reagents and solvents were purchased from commercial sources and were used without further purification. Silica gel column chromatography was performed using silica gel (32-63 μ). Preparative thin-layer chromatography (PTLC) separations were carried out on 1000μ AnalTech thin layer chromatography plates (Lot No. 13401).

(2E,6E)-2,6-Bis((5-methylisoxazol-3-yl)methylene)cyclohexanone (general formula (I), 5BHR-124 side group, shown as Compound 8 in Table 4) was prepared in 49% yield as a yellow crystal: mp. 155-156° C. IR (neat) $v_{max}$: 3129, 2943, 1685, 1636, 1598, 1426, 1267, 1181, 910, 783 $cm^{-1}$. $^1H$ NMR (300 MHz, $CD_3Cl$) δ. 2.47 (s, 6H), 2.52 (s, 3H), 3.90 (s, 4H), 6.11 (s, 2H), 7.42 (s, 2H). $^{13}C$ NMR (75 MHz, $CD_3Cl$) δ. 12.2, 45.7, 57.5, 103.6, 121.9, 138.1, 158.8, 169.9, 186.5. HR-MS (ESI) m/z: calcd for $C_{16}H_{18}N_3O_3$ [M+H]: 300.1348. found 300.1345.

Example 2

Synthesis of (2E,6E)-2,6-Bis((5-methylisoxazol-3-yl)methylene)cyclohexanone (General Formula (II), Side Group 5BHR-124, Shown as Compound 18 in Table 4)

Sodium methoxide in methanol (5.4 M, 0.14 mL, 0.75 mmol) was added to a solution of 5-methylisoxazole-3-carbaldehyde (166.5 mg, 1.5 mmol) and cyclohexanone (73.5 mg, 0.75 mmol) in methanol (10 mL), and the mixture was stirred for 4 h-18 h and monitored with TLC. When the reaction was completed, saturated solution of ammonium chloride was added, and the subsequent mixture was extracted with dichloromethane. The organic layer was dried over anhydrous $MgSO_4$. The solvent was evaporated under vacuum to give a crude product, which was purified by preparative TLC (5% methanol in dichloromethane).

NMR spectra were obtained on a Bruker Fourier 300 spectrometer in CDC3, CD3OD, or DMSO-d6. The chemical shifts are given in d (ppm) referenced to the respective solvent peak, and coupling constants are reported in Hz. All reagents and solvents were purchased from commercial sources and were used without further purification. Silica gel column chromatography was performed using silica gel (32-63 µ). Preparative thin-layer chromatography (PTLC) separations were carried out on 1000µ AnalTech thin layer chromatography plates (Lot No. 13401).

(2E,6E)-2,6-Bis((5-methylisoxazol-3-yl)methylene)cyclohexanone (general formula (II), side group 5BHR-124, shown as Compound 18 in Table 4) was prepared in 41.5% yield as a yellow solid: mp. 188-188.5° C. IR (neat) $v_{max}$: 3112, 2960, 1681, 1590, 1451, 1428, 1309, 1258, 1168, 1138 cm$^{-1}$. $^1$H NMR (300 MHz, CDC$_3$) δ. 1.88 (quin, J=6.3 Hz, 2H), 2.47 (s, 6H), 3.07 (t, J=6.3 Hz, 4H), 6.15 (s, 2H), 7.49 (s, 2H). $^{13}$C NMR (75 MHz, CDC$_3$) δ. 12.2, 21.4, 28.9, 103.4, 123.5, 140.9, 159.4, 169.6, 189.2. HR-MS (ESI) m/z: calcd for $C_{16}H_{17}N_2O_3$ [M+H]: 285.1239. found 285.1229.

Example 3

Synthesis of (1E,4E)-1,5-Bis(3-methylisoxazol-5-yl) penta-1,4-dien-3-one (General Formula (III), 5BHR-136 Side Group, Shown as Compound 28 in Table 4)

The reaction mixture of 3-methylisoxazole-5-carbaldehyde (444 mg, 4 mmol), acetone (116 mg, 2 mmol) and K$_2$CO$_3$ (1.104 g, 4 mmol) in the mixed solvent of toluene-ethanol-water (10 mL+4.0 mL+2.0 mL) was stirred at 70° C. for 12 h. After cooling down to room temperature, the solvent was evaporated in vacuo. The resulting residue was partitioned between dichloromethane and water. The aqueous phase was further extracted with dichloromethane twice. The combined organic extracts were rinsed with brine and dried over anhydrous magnesium sulfate. The organic solvent was removed under vacuum to give a residue, which was purified by preparative TLC (5% methanol in dichloromethane).

NMR spectra were obtained on a Bruker Fourier 300 spectrometer in CDC$_3$, CD$_3$OD, or DMSO-d$_6$. The chemical shifts are given in d (ppm) referenced to the respective solvent peak, and coupling constants are reported in Hz. All reagents and solvents were purchased from commercial sources and were used without further purification. Silica gel column chromatography was performed using silica gel (32-63 µ). Preparative thin-layer chromatography (PTLC) separations were carried out on 1000µ AnalTech thin layer chromatography plates (Lot No. 13401).

(1E,4E)-1,5-Bis(3-methylisoxazol-5-yl)penta-1,4-dien-3-one (general formula (III), 5BHR-136 side group, shown as Compound 28 in Table 4) was prepared in 26% yield as a yellow crystal: mp. 167-169° C. IR (neat) $v_{max}$: 3112, 2925, 1677, 1642, 1609, 1573, 1414, 1091, 994 cm$^{-1}$. $^1$H NMR (300 MHz, CDC$_3$) δ. 2.37 (s, 6H), 6.41 (s, 2H), 7.18 (d, J=15.9 Hz, 2H), 7.50 (d, J=15.9 Hz, 2H). $^{13}$C NMR (75 MHz, CDC$_3$) δ. 11.4, 108.1, 126.5, 128.8, 160.6, 165.4, 187.2. HR-MS (ESI) m/z: calcd for $C_{13}H_{13}N_2O_3$ [M+H]: 245.0926. found 245.0921.

E. BIOLOGICAL EFFECTS OF THE CURCUMIN ANALOGS HAVING A SCAFFOLD REPRESENTED BY ONE OF GENERAL FORMULAS (I)-(IV)

The compounds of this invention have been found to decrease the viability of aggressive human cancer cells. Also, the compounds of this invention have been found to inhibit the growth of the aggressive human cancer cells. As such, this invention contemplates using the claimed compounds to decrease the viability of aggressive human cancer cells, as well as to inhibit the growth of the aggressive human cancer cells. In one embodiment, the present invention provides a method of decreasing the viability of aggressive human cancer cells and inhibiting the growth of the aggressive human cancer cells by administering an effective amount of a curcumin analog compound having a scaffold represented as one of general formulas (I)-(IV), and two side groups, each independently chosen from the side groups listed in Tables 1-3.

1. Curcumin Analog Compounds can Decrease Aggressive Human Cancer Cell Viability The viability decrease in human cancer cells can be readily determined by any one of several assays and techniques known to those of ordinary skill in the art. These assays and techniques can use cells from any one of various aggressive human cancer cell lines. The HeLa cervical cancer cell line is a well-known aggressive human cancer cell line.

In one assay, HeLa cervical cancer cells were cultured with selected curcumin analogs in solution concentrations of either 10 µM and 1 µM, for between three days and five days, while equal treatment volumes of DMSO were used as vehicle control. Cell numbers were counted with a cell viability analyzer (Beckman-Coulter). The ratio of drug treated viable cell numbers to control vehicle (DMSO) treated viable cell numbers was defined as percentage viability. Several curcumin analogs having scaffolds represented by one of general formulas (I)-(III) and side groups selected from Tables 1-3 show significant ability to decrease the viability of HeLa cervical cancer cells. Compound nos. 5-9 and 14-46 (see Table 4) decrease the number of HeLa cervical cancer cells still alive after three days.

Example 4

Curcumin Analog Compounds Decrease Viability of HeLa Cervical Cancer Cells

As shown in Table 5, the indicated curcumin analog compounds at concentrations of 10 µM and 1 µM have differing effects on HeLa cervical cancer cell viability when administered to HeLa cervical cancer cells. The "ND" shown in Table 5 represents "no data" for the indicated compounds at the indicated solution concentration. An "ND" finding was recorded when an analog already showed excellent inhibition at the 1 µM lower concentration, and there was no reason to test the analog's inhibitory activity at the 10 µM higher concentration.

The HeLa cells used in the experiments summarized by Table 5 were cultured in RPMI-1640 medium supplemented with 10% FBS, 4 mM glutamine, 1 mM sodium pyruvate, 100 IU/mL penicillin, 100 ug/mL streptomycin and 0.25 ug/mL amphotericin. The HeLa cells were plated in 24-well plates at a density of 20,000 cells in each well in 10% FBS RPMI-1640. The HeLa cells were then treated with curcumin, or synthesized curcumin analogs separately at 10 µM and 1 µM for three days, while equal treatment volumes of DMSO were used as vehicle control. Cell numbers were counted with a cell viability analyzer (Beckman-Coulter).

As shown in Table 5, compound nos. 5-9, and 14-46 decrease the number of HeLa cervical cancer cells still alive after three days. Specifically, compound nos. 8, 43-46 can reduce significantly the percentage viability of HeLa cervical cancer cells. As shown in Table 5, the ratio of drug treated viable cell numbers to control vehicle (DMSO) treated viable cell numbers was defined as percentage viability.

As shown in Table 5, compound No. 8, having a scaffold represented by general formula (I), with two side groups both being the structure represented by 5BHR-85 (Table 1), decreases HeLa cervical cancer cell viability down to 19% viability at compound concentration 1 μM, and to 12.8% viability at compound concentration 10 μM. Compound No. 43, having a scaffold represented by general formula (III), with two side groups both being the structure represented by BBHR-1039 (Table 3), decreases HeLa cervical cancer cell viability down to 8.2% viability at compound concentration 1 μM, and to 4.7% viability at compound concentration 10 μM. Compound No. 44, having a scaffold represented by general formula (III), with two side groups both being the structure represented by BBHR-1040 (Table 3), decreases HeLa cervical cancer cell viability down to 2.5% viability at compound concentration 1 μM, and to 2.1% viability at compound concentration 10 μM. Compound No. 45, having a scaffold represented by general formula (III), with two side groups both being the structure represented by BBHR-1041 (Table 3), decreases HeLa cervical cancer cell viability down to 8.2% viability at compound concentration 1 μM, and to 1.4% viability at compound concentration 10 μM. Compound No. 46, having a scaffold represented by general formula (III), with two side groups both being the structure represented by BBHR-1027 (Table 3), decreases HeLa cervical cancer cell viability down to 2.5% viability at compound concentration 1 μM, and to an undetermined percentage at 10 μM.

TABLE 5

In vitro cell viability data of curcumin analogs as administered to HeLa cells

| Curcumin Analog No. (as listed in Table 4) | HeLa Cell viability after treatment with analog (% viability) | |
| --- | --- | --- |
| | 10 μM | 1 μM |
| curcumin | 42.5 | 100 |
| 1 | 118.5 | 126.94 |
| 2 | 95.9 | 111.1 |
| 3 | 97.8 | 100.9 |
| 4 | 67.4 | 107.1 |
| 5 | 21.6 | 51.7 |
| 6 | 12.0 | 72.0 |
| 7 | 59.5 | 59.5 |
| 8 | 12.8 | 19 |
| 9 | 27.8 | 75.3 |
| 10 | 85.1 | 114.9 |
| 11 | 100 | 100 |
| 12 | 94.5 | 100 |
| 13 | 100 | 97 |
| 14 | 71.4 | 88 |
| 15 | 9.7 | 78 |
| 16 | 15.8 | 79 |
| 17 | 59.5 | 100 |
| 18 | 15.9 | 32 |
| 19 | 15.9 | 95 |
| 20 | 11.4 | 35 |
| 21 | 17.7 | 81.8 |
| 22 | 23.1 | 34.1 |
| 23 | 82.6 | 59 |
| 24 | 19.2 | 68 |
| 25 | 13.7 | 89 |
| 26 | 65.9 | 100 |
| 27 | 15.9 | 48 |
| 28 | ND | 28 |
| 29 | ND | 77 |
| 30 | ND | 67 |
| 31 | ND | 52 |
| 32 | ND | 3.4 |
| 33 | ND | 3.0 |
| 34 | ND | 7.7 |
| 35 | ND | 6.1 |
| 36 | ND | 25.6 |
| 37 | ND | 72.9 |
| 38 | ND | 92.8 |
| 41 | ND | 5.72 |
| 43 | 4.7 | 8.2 |
| 44 | 2.1 | 2.5 |
| 45 | 1.4 | 8.2 |
| 46 | ND | 2.5 |

2. Curcumin Analogs Show Cytotoxicity Against Aggressive Human Cancer Cell Viability.

The half maximal inhibitory concentration ($IC_{50}$) is a measure of the effectiveness of a substance in inhibiting a specific biological or biochemical function. It is commonly used as a measure of antagonist drug potency. For the claimed invention, the $IC_{50}$ is the concentration which inhibits growth of 50% of the tested cells. As shown in Tables 6-8, the $IC_{50}$ number is the drug concentration effective at inhibiting growth of 50% of the tested cells. Tables 6-8 show the in vitro cytotoxicity of curcumin analogs towards cells from aggressive human cancer cells from: cell line DU-14, a human androgen independent prostate cancer cell line, cell line PC-3, a human androgen independent prostate cancer cell line, and cell line HeLa, a human cervical cancer cell line. The curcumin analogs are effective at inhibiting the growth of aggressive human cancer cells, such as prostate cancer cells and cervical cancer cells.

Among twenty eight heteroaromatic analogs of curcumin that have been prepared and evaluated, twenty four analogs showed better cytotoxicity towards both PC-3 and DU-145 androgen-independent prostate cancer cell lines relative to curcumin. As shown in Tables 6-8, the $IC_{50}$ values of these twenty four analogs against PC-3 cells and DU-145 cells are significantly lower than that of curcumin.

Among the analogs having one of the four scaffolds that have been prepared and evaluated, all compounds, except compound no. 26 (see Table 4), that contain the scaffold represented by general formula (III) with acetone as a linker showed excellent cytotoxicity against both PC-3 and DU-145 prostate cancer cell lines with optimum $IC_{50}$ value as 16 nM against DU-145 cells and 33 nM against PC-3 cells. The analogs containing the scaffold represented by general formula (III) are optimally 19 times more potent than curcumin against DU-145 cells and optimally 60 times more potent than curcumin against PC-3 cells.

Among forty three heteroaromatic analogs of curcumin that have been prepared and evaluated, thirty analogs showed stronger ability to decrease HeLa cell viability at both 1 μM and 10 μM concentrations than curcumin. As shown in Table 8, the $IC_{50}$ values of fourteen analogs (compound nos. 6, 8, 18, 20, 21, 22, 27, 28, 32, 33, 34, 35, 41, and 46) against the HeLa cervical cancer cells were measured, indicating that these fourteen analogs are between 13 times and 51 times more cytotoxically potent towards the HeLa cervical cancer cells than curcumin.

Three of the most promising curcumin analogs, compound nos. 21, 22, and 28, were selected for further evaluation of their cytotoxicity towards metastatic breast cancer cells from cellline MDA-MB-231 and metastatic non-small cell lung cancer cells from cell line A549. As shown in Table 9, these three curcumin analogs are between 6 times and 7 times more potent than curcumin against MDA-MB-231 breast cancer cells. As shown in Table 10, these three curcumin analogs are between 94 times and 150 times more potent than curcumin against A549 non-small cell lung cancer cells.

Figure 9:
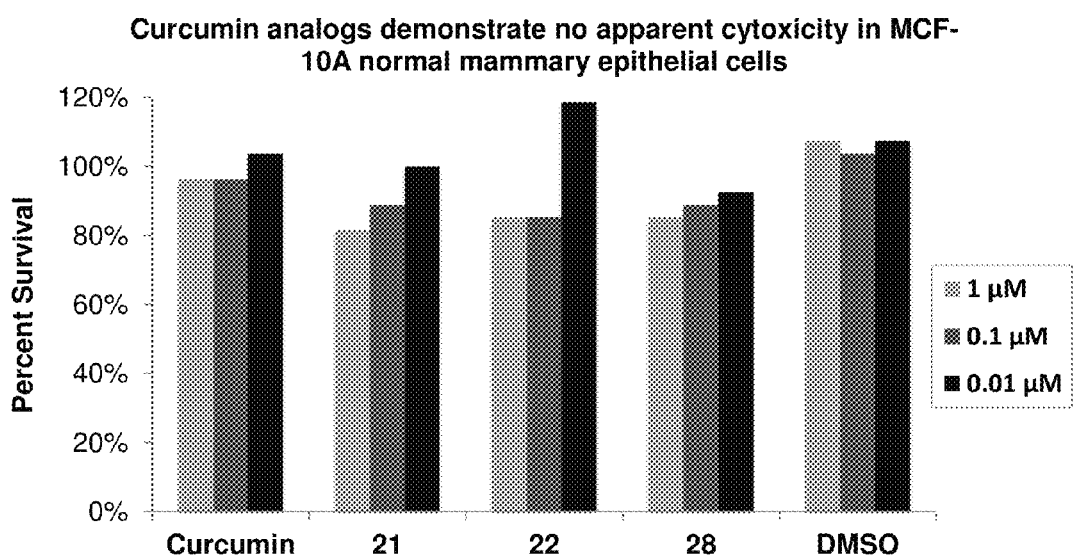
FIG. 9 shows a bar graph displaying data showing no apparent cytotoxicity of curcumin, compound nos. 21, 22, and 28 toward non-cancerous MCF-10A mammary epithelial cells.

Curcumin is selectively toxic towards aggressive cancer cells, and is non-toxic towards non-cancerous cells. As shown in FIG. 9, compound nos. 21, 22, and 28 demonstrate no apparent cytotoxicity towards non-cancerous MCF-10A normal mammary epithelial cells.

Example 5

Curcumin Analog Compounds Inhibit Growth of PC-3 Prostate Cancer Cells

As shown in Table 6, curcumin analog compounds having a scaffold represented by general formulas (I)-(III) are effective at inhibiting the growth of aggressive prostate cancer cells.

For the experiments summarized in Table 6, the PC-3 prostate cancer cells were routinely cultured in RPMI-1640 medium supplemented with 10% FBS, 4 mM glutamine, 1 mM sodium pyruvate, 100 IU/mL penicillin, 100 ug/mL streptomycin and 0.25 ug/mL amphotericin. Cell cultures were maintained in 5% carbon dioxide at a temperature of 37° C. The PC-3 cells were plated in 24-well plates at a density of 20,000 each well in 10% FBS RPMI-1640 or DMED medium. The PC-3 cells then were treated with curcumin, or synthesized curcumin analogs separately at 10 μM and 1 μM for five days, while equal treatment volumes of DMSO were used as vehicle control. Cell numbers were counted with a cell viability analyzer (Beckman-Coulter). As shown in Table 6, the $IC_{50}$ values were obtained from dose-response curves for each curcumin analog. A preliminary dose response curve was prepared from the collected data by means well known to those of ordinary skill in the art.

As shown in Table 6, the PC-3 prostate cancer cells were further exposed to the indicated analogs at six different concentrations for five days to determine the $IC_{50}$ value. The six different concentrations fell within a selected linear concentration range determined by reference to the preliminary dose response curve and efforts to estimate the concentration at which 50% of the cell growth would be inhibited. The selected six different concentrations were used to further fill out the dose response curve to pinpoint a more exact $IC_{50}$ value.

TABLE 6

In vitro cytotoxicity ($IC_{50}$, nM) of curcumin analogs against PC-3 prostate cancer cells

| Curcumin Analog No. (as listed in Table 4) | $IC_{50}$ (nM) | $IC_{50}$ (curcumin)/ $IC_{50}$ (analog) |
|---|---|---|
| curcumin | 1980 | 1 |
| 1 | 110 | 18 |
| 2 | 6630 | 0.3 |
| 3 | 76000 | 0.03 |
| 4 | 1020 | 1.9 |
| 5 | 420 | 4.7 |
| 6 | 800 | 2.5 |
| 7 | 310 | 6.4 |
| 8 | 140 | 14 |
| 9 | 130 | 15 |
| 10 | 160 | 12 |

TABLE 6-continued

In vitro cytotoxicity ($IC_{50}$, nM) of curcumin analogs against PC-3 prostate cancer cells

| Curcumin Analog No. (as listed in Table 4) | $IC_{50}$ (nM) | $IC_{50}$ (curcumin)/ $IC_{50}$ (analog) |
|---|---|---|
| 11 | 830 | 2 |
| 12 | 470 | 4.2 |
| 13 | 130000 | 0.015 |
| 14 | 260 | 7.6 |
| 15 | 110 | 18 |
| 16 | 120 | 16.5 |
| 17 | 1970 | 1 |
| 18 | 71 | 28 |
| 19 | 54 | 37 |
| 20 | 89 | 22 |
| 21 | 63 | 31 |
| 22 | 46 | 43 |
| 23 | 1900 | 15 |
| 24 | 68 | 29 |
| 25 | 94 | 21 |
| 26 | 840 | 2.4 |
| 27 | 250 | 7.9 |
| 28 | 41 | 48 |

As shown in Table 6, the $IC_{50}$ (curcumin)/$IC_{50}$ (analog) ratio describes the difference in pharmacologic activity between two similar compounds. A high $IC_{50}$ (curcumin)/$IC_{50}$ (analog) ratio correlates with a high inhibition efficacy for the curcumin analog compound. An $IC_{50}$ (curcumin)/$IC_{50}$ (analog) ratio of 2 means that the analog compound can inhibit the viability of 50% of the PC-3145 prostate cancer cells at only 50% of the curcumin concentration necessary to do so, or that the analog compound is twice as potent as curcumin.

As shown in Table 6, compound nos. 1, 4-12, 14-28 can inhibit PC-3 prostate cancer cell viability by 50% at low concentrations—defined as concentrations below the necessary curcumin concentration of 1980 nM to inhibit growth of 50% of the PC-3 cells. This shows that compound nos. 1, 4-12, 14-28 at low concentrations are effective at limiting the growth of androgen independent prostate cancer cells, such as PC-3 cells.

As shown in Table 6, compound nos. 1, 4-12, 14-28 all have $IC_{50}$ (curcumin)/$IC_{50}$ (analog) ratios greater than 1 when tested against PC-3 cells. Compound no. 2 shows an $IC_{50}$ (curcumin)/$IC_{50}$ (analog) ratio of 18 for PC-3 prostate cancer cells. Compound no. 2 can accomplish curcumin's inhibiting effect for PC-3 prostate cancer cells at 1/18 curcumin's concentration, and is 18 times as potent as curcumin. Compound nos. 2, 8-10, 18-25 and 28 all have $IC_{50}$ (curcumin)/$IC_{50}$ (analog) ratio greater than 10, so these compounds can accomplish the inhibitory effect of curcumin on PC-3 prostate cancer cells at less than 1/10 curcumin's concentration, and is at least 10 times as potent as curcumin.

Example 6

Curcumin Analog Compounds Inhibit Growth of DU-145 Prostate Cancer Cells

As shown in Table 7, curcumin analog compounds having a scaffold represented by general formulas (I)-(III) are effective at inhibiting the growth of aggressive prostate cancer cells.

The DU-145 prostate cancer cells were cultured in phenol red-free DMEM supplemented with 10% FBS, 4 mM glutamine, 1 mM sodium pyruvate, 100 IU/mL penicillin, 100 ug/mL streptomycin and 0.25 ug/mL amphotericin. DU-145 cells were plated in 24-well plates at a density of 20,000 cells in each well in 10% FBS RPMI-1640. The cells were then treated with curcumin, or synthesized curcumin analogs separately at 10 μM and 1 μM for five days, while equal treatment volumes of DMSO were used as vehicle control. Cell numbers were counted with a cell viability analyzer (Beckman-Coulter).

As shown in Table 7, the $IC_{50}$ values were obtained from dose-response curves for each curcumin analog. A preliminary dose response curve was prepared from the collected data by means well known to those of ordinary skill in the art.

As shown in Table 7, the DU-145 cells were further exposed to the indicated analogs at six different concentrations for five days to determine the $IC_{50}$ value. The six different concentrations fell within a selected linear concentration range determined by reference to the preliminary dose response curve and efforts to estimate the concentration at which 50% of the cell growth would be inhibited. The selected six different concentrations were used to further fill out the dose response curve to pinpoint a more exact $IC_{50}$ value.

$IC_{50}$ values were obtained from dose-response curves for each curcumin analog. The $IC_{50}$ (curcumin)/$IC_{50}$ (analog) ratio describes the difference in pharmacologic activity between two similar compounds. A high $IC_{50}$ (curcumin)/$IC_{50}$ (analog) ratio correlates with a high inhibition efficacy for the curcumin analog compound. An $IC_{50}$ (curcumin)/$IC_{50}$ (analog) ratio of 2 means that the analog compound can inhibit the viability of 50% of the DU-145 prostate cancer cells at only 50% of the curcumin concentration necessary to do so, or that the analog compound is twice as potent as curcumin.

As shown in Table 7, compound nos. 1, 2, 5-8, 10, 11, 15-18, 20-25, 27 and 28 can inhibit 50% of growth of DU-145 prostate cancer cell at low concentrations—defined as concentrations below the necessary curcumin concentration of 300 nM to inhibit 50% of the growth of DU-145 cells. This shows that compound nos. 1, 2, 5, 7, 8, 10, 11, 15, 16, 18, 20-25, 27 and 28 at low concentrations are effective at limiting the growth of androgen independent prostate cancer cells.

Compounds 1, 2, 5, 7, 8, 10, 11, 15, 16, 18, 20-25, 27 and 28 all have $IC_{50}$ (curcumin)/$IC_{50}$ (analog) ratios greater than 1 for DU-145 cells. According to Table 7, compound no. 2 shows an $IC_{50}$ (curcumin)/$IC_{50}$ (analog) ratio of 30 for DU-145 cells. Compound no. 2 can accomplish curcumin's inhibiting effect for DU-145 at about 1/30 concentration, and is 30 times as potent as curcumin. Compound no. 28 shows an $IC_{50}$ (curcumin)/$IC_{50}$ (analog) ratio of 18.8 for DU-145 cells. Compound no. 28 can accomplish curcumin's inhibiting effect for DU-145 at about 1/19 concentration, and is 19 times as potent as curcumin.

TABLE 7

In vitro cytotoxicity ($IC_{50}$, nM) of curcumin analogs against DU-145 human cancer cells

| Curcumin Analog No. (as listed in Table 4) | $IC_{50}$ (nM) | $IC_{50}$ (curcumin)/ $IC_{50}$ (analog) |
|---|---|---|
| curcumin | 300 | 1 |
| 1 | 140 | 2.1 |
| 2 | 10 | 30 |
| 3 | 1870000 | 0.0002 |
| 4 | 1640 | 0.18 |
| 5 | 46 | 6.5 |
| 6 | 430 | 0.7 |
| 7 | 76 | 3.9 |
| 8 | 34 | 8.8 |
| 9 | 690 | 0.4 |
| 10 | 100 | 3 |
| 11 | 250 | 1.2 |
| 12 | 360 | 0.8 |
| 13 | 90000 | 0.003 |
| 14 | 730 | 0.41 |
| 15 | 120 | 2.5 |
| 16 | 75 | 4 |
| 17 | 1650 | 0.18 |
| 18 | 70 | 4.3 |
| 19 | 340 | 0.9 |
| 20 | 54 | 5.6 |
| 21 | 35 | 8.6 |
| 22 | 57 | 5.3 |
| 23 | 160 | 1.9 |
| 24 | 55 | 5.5 |
| 25 | 96 | 3 |
| 26 | 750 | 0.4 |
| 27 | 42 | 7.1 |
| 28 | 16 | 18.8 |

Example 7

Curcumin Analog Compounds Inhibit Growth of HeLa Cervical Cancer Cells

The HeLa cervical cancer cells were cultured in RPMI-1640 medium supplemented with 10% FBS, 4 mM glutamine, 1 mM sodium pyruvate, 100 IU/mL penicillin, 100 ug/mL streptomycin and 0.25 ug/mL amphotericin. HeLa cells were plated in 24-well plates at a density of 20,000 cells in each well in 10% FBS RPMI-1640. The cells were then treated with curcumin, or synthesized curcumin analogs separately at 10 μM and 1 μM for three days, while equal treatment volumes of DMSO were used as vehicle control. Cell numbers were counted with a cell viability analyzer (Beckman-Coulter). The ratio of drug treated viable cell numbers to vehicle treated viable cell numbers was defined as percentage viability. $IC_{50}$ values were obtained from dose-response curves for each curcumin analog.

As shown in Table 8, the $IC_{50}$ values were obtained from dose-response curves for each curcumin analog. A preliminary dose response curve was prepared from the collected data by means well known to those of ordinary skill in the art.

As shown in Table 8, the HeLa cells were further exposed to the indicated analogs at six different concentrations for three days to determine the $IC_{50}$ value. The six different concentrations fell within a selected linear concentration range determined by reference to the preliminary dose response curve and efforts to estimate the concentration at which 50% of the cell growth would be inhibited. The selected six different concentrations were used to further fill out the dose response curve to pinpoint a more exact $IC_{50}$ value.

The $IC_{50}$ experiments in HeLa human cervical cancer cells were only conducted using a few curcumin analogs: compound nos. 6, 8, 18, 20-22, 27-28, 32-35, 41 and 45. As shown in Table 8, compound nos. 6, 8, 18, 20-22, 27-28, 32-35, 41 and 45 all can inhibit 50% of HeLa cervical cancer cell growth at low concentrations—defined as concentrations below the necessary curcumin concentration of 10,456 nM to inhibit growth of 50% of the HeLa cells. This shows that compound nos. 6, 8, 18, 20-22, 27-28, 32-35, 41 and 45 at low concentrations are effective at limiting growth of human cervical cancer cells.

As shown in Table 8, compound nos. 6, 8, 18, 20-22, 27-28, 32-35, 41 and 45 all have $IC_{50}$ (curcumin)/$IC_{50}$ (analog) ratios greater than 13, so these compounds can accomplish the inhibitory effect of curcumin on HeLa cervical cancer cells at less than 1/13 curcumin's concentration, and have at least 13 times the potency of curcumin. Compound no. 8 shows an $IC_{50}$ (curcumin)/$IC_{50}$ (analog) ratio of 51 for HeLa cervical cancer cells. Compound no. 8 can accomplish curcumin's inhibiting effect for HeLa cervical cancer cells at 1/51 curcumin's concentration, and is 51 times as potent as curcumin. Compound no. 34 shows an $IC_{50}$ (curcumin)/$IC_{50}$ (analog) ratio of 70 for HeLa cervical cancer cells. Compound no. 34 can accomplish curcumin's inhibiting effect for HeLa cervical cancer cells at 1/70 curcumin's concentration, and is 70 times as potent as curcumin.

TABLE 8

In vitro cytotoxicity ($IC_{50}$, nM) of curcumin analogs against HeLa cervical cancer cells

| Curcumin Analog No. (as listed in Table 4) | $IC_{50}$ (nM) | $IC_{50}$ (curcumin)/ $IC_{50}$ (analog) |
|---|---|---|
| curcumin | 10456 | 1 |
| 1 | | |
| 2 | | |
| 3 | | |
| 4 | | |
| 5 | | |
| 6 | 817 | 13 |
| 7 | | |
| 8 | 205 | 51 |
| 9 | | |
| 10 | | |
| 11 | | |
| 12 | | |
| 13 | | |
| 14 | | |
| 15 | | |
| 16 | | |
| 17 | | |
| 18 | 552 | 19 |
| 19 | | |
| 20 | 418 | 25 |
| 21 | 654 | 16 |
| 22 | 430 | 24 |
| 23 | | |
| 24 | | |
| 25 | | |
| 26 | | |
| 27 | 296 | 35 |
| 28 | 226 | 46 |
| 29 | | |
| 30 | | |
| 31 | | |
| 32 | 250 | 42 |
| 33 | 230 | 46 |
| 34 | 150 | 70 |
| 35 | 590 | 18 |
| 36 | | |
| 37 | | |
| 38 | | |
| 41 | 321 | 33 |
| 43 | | |
| 44 | | |
| 45 | 696 | 15 |

Based on the results summarized in Tables 6-8, three promising compounds were further tested. Compound nos. 21, 22, and 28 were further tested on other aggressive human cancer cells lines. These three compounds were selected because they showed most potent cytotoxicity against both PC-3 and DU-145 prostate cancer cell lines simultaneously. Compound nos. 21, 22, and 28 were selected for further evaluation of their cytotoxicity towards the human metastatic breast cancer cell line (MDA-MB-231) and the human metastatic non-small cell lung cancer line (A549).

Example 8

Compound Nos. 21, 22 and 28 Inhibit Growth of MDA-MB-231 Breast Cancer Cells

The MDA-MB-231 breast cancer cells were cultured in RPMI-1640 medium supplemented with 10% FBS, 4 mM glutamine, 1 mM sodium pyruvate, 100 IU/mL penicillin, 100 ug/mL streptomycin and 0.25 ug/mL amphotericin. MDA-MB-231 cells were plated in 24-well plates at a density of 20,000 cells in each well in 10% FBS RPMI-1640. The cells were then treated with curcumin, or synthesized curcumin analogs separately at 10 μM and 1 μM for five days, while equal treatment volumes of DMSO were used as vehicle control. Cell numbers were counted with a cell viability analyzer (Beckman-Coulter). The ratio of drug treated viable cell numbers to vehicle treated viable cell numbers was defined as percentage viability. $IC_{50}$ values were obtained from dose-response curves for each curcumin analog.

As shown in Table 9, curcumin analog compound no. 21 is about seven times more potent than curcumin towards MDA-MB-231 cells. Compound no. 22 is about six times more potent than curcumin towards MDA-MB-231 cells. Compound no. 28 is about seven times more potent than curcumin towards MDA-MB-231 cells.

TABLE 9

In vitro cytotoxicity ($IC_{50}$, μM) of selective curcumin analogs toward MDA-MB-231 cells

| Curcumin Analog No. (as listed in Table 4) | $IC_{50}$ (analog) | $IC_{50}$ (curcumin)/ $IC_{50}$ (analog) |
|---|---|---|
| curcumin | 880 | 1 |
| 21 | 130 | 6.8 |
| 22 | 150 | 5.9 |
| 28 | 156 | 5.6 |

Example 9

Compound Nos. 21, 22 and 28 Inhibit Growth of A549 Non-Small Cell Lung Cancer Cells The A549 non-small cell lung cancer cells were cultured in RPMI-1640 medium supplemented with 10% FBS, 4 mM glutamine, 1 mM sodium pyruvate, 100 IU/mL penicillin, 100 ug/mL streptomycin and 0.25 ug/mL amphotericin. A549 non-small cell lung cancer cells were plated in 24-well plates at a density of 20,000 cells in each well in 10% FBS RPMI-1640 or DMED medium. The cells were then treated with curcumin, or synthesized curcumin analogs separately at 10 μM and 1 μM for between three and five days, while equal treatment volumes of DMSO were used as vehicle control. Cell numbers were counted with a cell viability analyzer (Beckman-Coulter). The ratio of drug treated viable cell numbers to vehicle treated viable cell numbers was defined as percentage viability. IC$_{50}$ values were obtained from dose-response curves for each curcumin analog.

As shown in Table 10, curcumin analog compound no. 21 is about 150 times more potent than curcumin towards A549 cells. Compound no. 22 is about 136 times more potent than curcumin towards A549 cells. Compound no. 28 is about 94 times more potent than curcumin towards A549 cells.

TABLE 10

In vitro cytotoxicity (IC$_{50}$, μM) of selective curcumin analogs toward A549 cells

| Curcumin Analog No. (as listed in Table 4) | IC$_{50}$ (analog) | IC$_{50}$ (curcumin)/ IC$_{50}$ (analog) |
|---|---|---|
| curcumin | 15000 | 1 |
| 21 | 100 | 150 |
| 22 | 110 | 136 |
| 28 | 160 | 93.8 |

Example 10

Several Curcumin Analogs are Shown to be Non-Toxic Towards Non-Cancerous Mammary Epithelial Cells The MCF-10A normal mammary epithelial cells were cultured in RPMI-1640 medium supplemented with 10% FBS, 4 mM glutamine, 1 mM sodium pyruvate, 100 IU/mL penicillin, 100 ug/mL streptomycin and 0.25 ug/mL amphotericin. The MCF-10A cells were plated in 24-well plates at a density of 20,000 each well in 10% FBS RPMI-1640 or DMED medium. The cells were then treated with curcumin, or the synthesized curcumin analogs separately at 10 μM, 1 μM, 0.1 μM for five days, while equal treatment volumes of DMSO were used as vehicle control. Cell numbers were counted with a cell viability analyzer (Beckman-Coulter).

As shown in FIG. 9, curcumin analog compound nos. 21, 22, and 28, demonstrate no apparent cytotoxicity towards MCF-10A normal mammary epithelial cells at any one of three concentrations 1 μM, 0.1 μM, and 0.01 μM. At all three concentrations, the three compounds do not reduce MCF-10A cell viability below 80%.

As shown in FIG. 9, at a concentration of 1 μM, curcumin allows the survival of about 95% of MCF-10A cells, compound no. 21 allows the survival of about 80% of MCF-10A cells, compound no. 22 allows the survival of about 85% of MCF-10A cells, and compound no. 28 allows the survival of about 85% of MCF-10A cells. Also as shown in FIG. 9, at a concentration of 0.1 μM, curcumin allows the survival of about 95% of MCF-10A cells, compound no. 21 allows the survival of about 90% of MCF-10A cells, compound no. 22 allows the survival of about 85% of MCF-10A cells, and compound no. 28 allows the survival of about 90% of MCF-10A cells. Also as shown in FIG. 9, at a concentration of 0.01 μM, curcumin allows the survival of 100% of MCF-10A cells and the growth thereof, compound no. 21 allows the survival of 100% of the MCF-10A cells, compound no. 22 allows the survival of 100% of MCF-10A cells and the growth thereof, and compound no. 28 allows the survival of about 90% of MCF-10A cells.

A number of embodiments of the invention have been described. Nevertheless, it will be understood by one of ordinary skill in the art that various modifications may be made without departing from the spirit and scope of the invention. Accordingly, other embodiments are within the scope of the present invention.

I claim:

1. A method for decreasing the viability of aggressive mammalian prostate cancer cells and inhibiting growth of said aggressive mammalian prostate cancer cells, comprising administering an effective amount of at least one curcumin analog having a scaffold represented by one of general formulas (III) and (IV) to said aggressive mammalian prostate cancer cells:

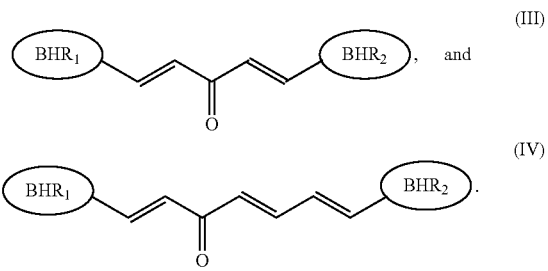

wherein each of BHR$_1$ and BHR$_2$ is a five-membered basic heteroaromatic ring group or a benzo-fused five-membered basic heteroaromatic ring group, wherein said five membered heteroaromatic ring group or said benzo-fused five-membered basic heteroaromatic ring group is unsubstituted or substituted with a C1-C6 saturated alkyl group or a C3-C6 cycloalkyl group, and wherein BHR$_1$ and BHR$_2$ are identical.

2. A method according to claim 1, wherein said BHR$_1$ and said BHR$_2$ independently is a member selected from the group consisting of:

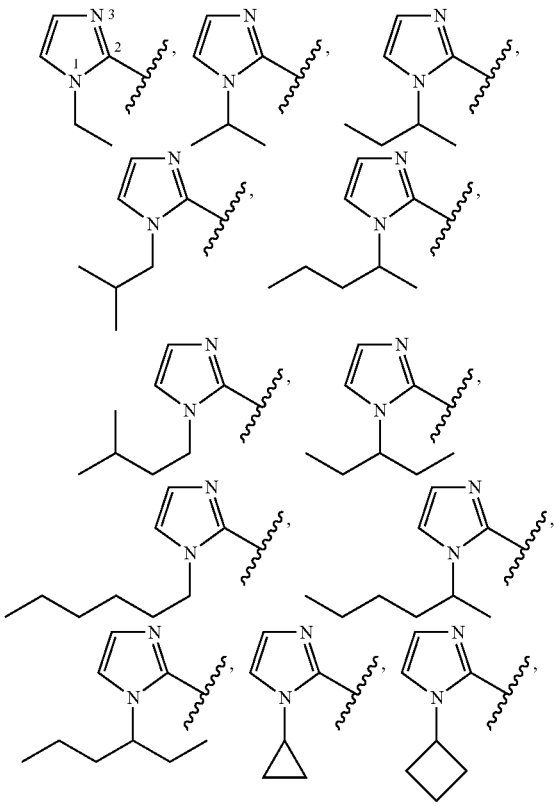

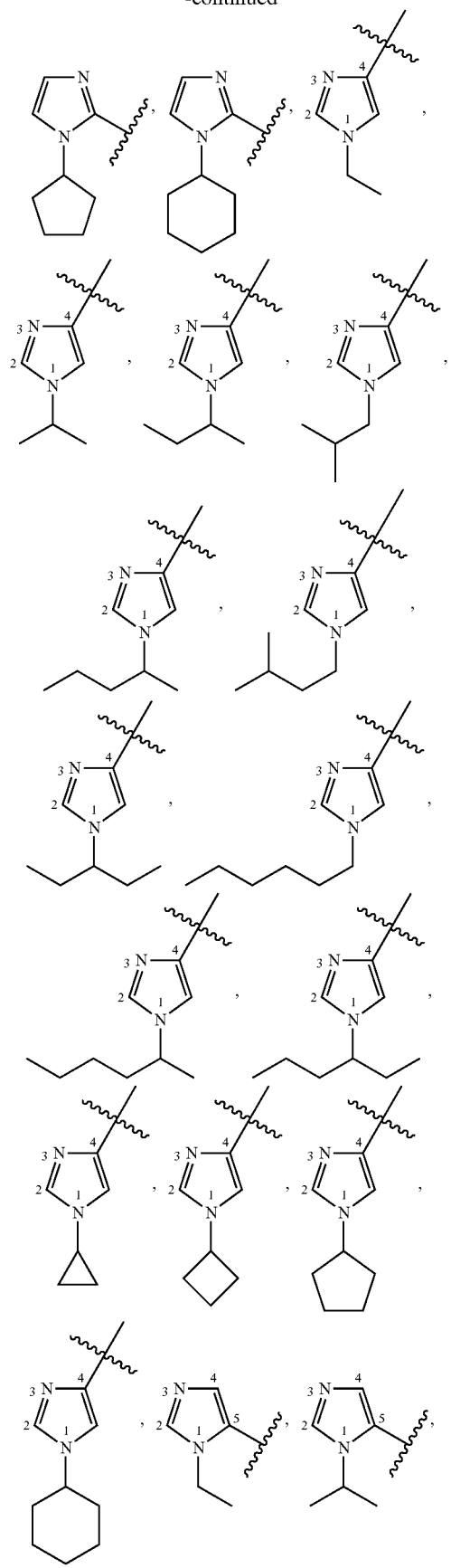
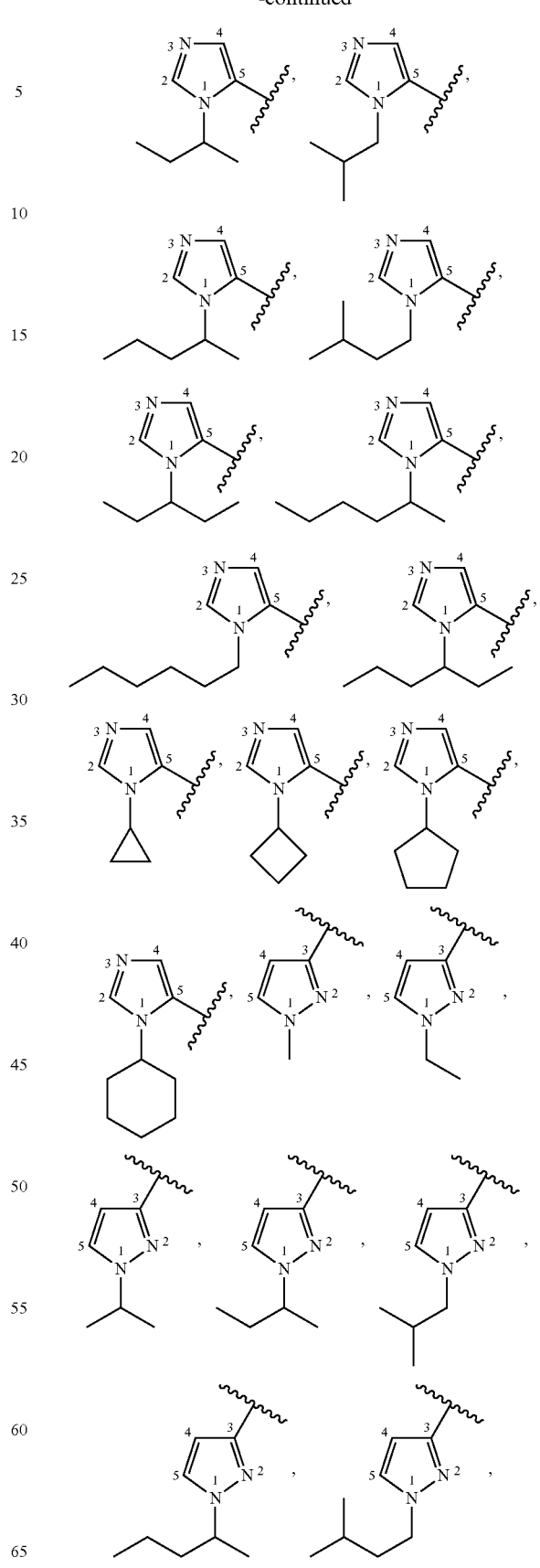

-continued
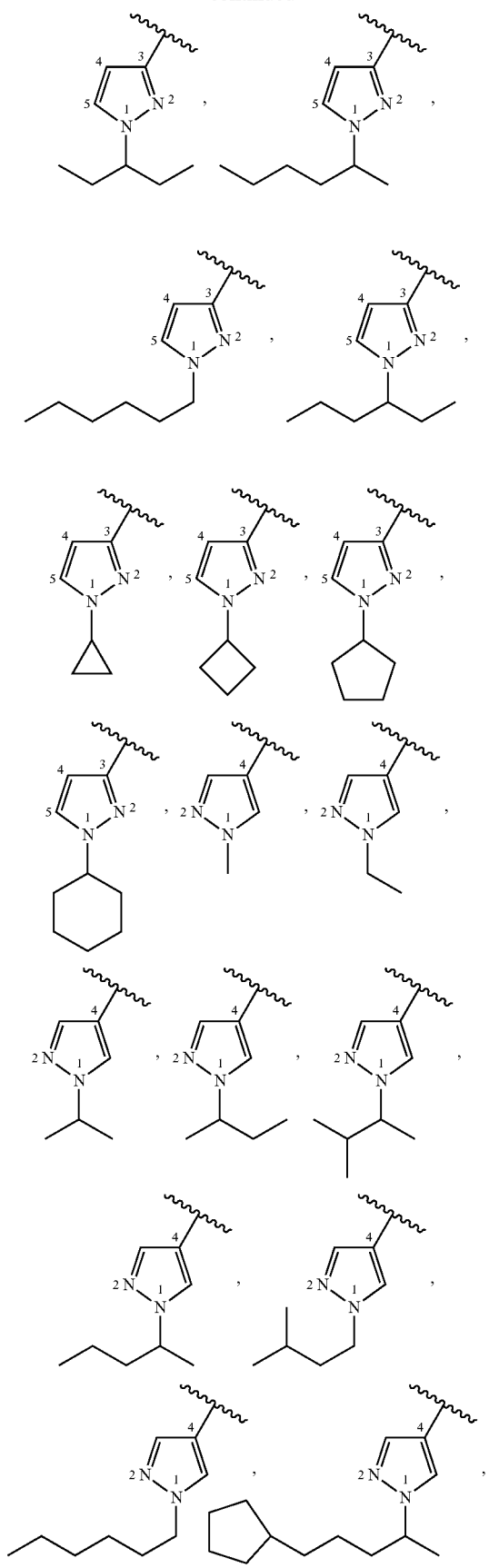
-continued
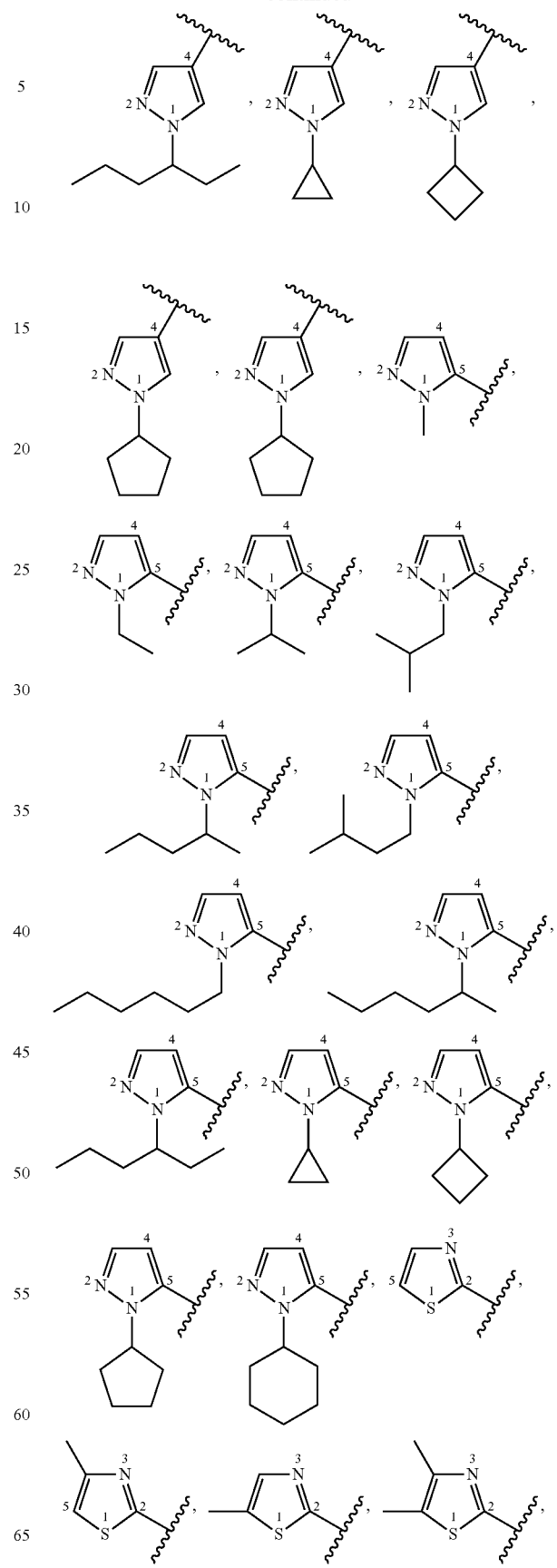

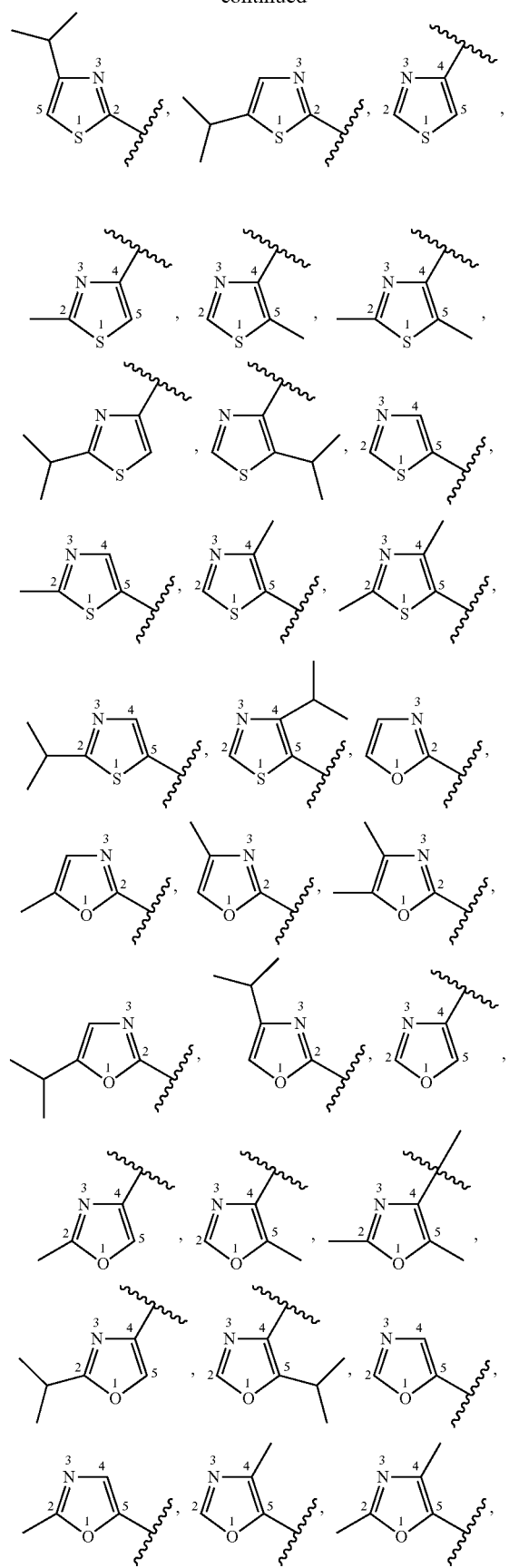
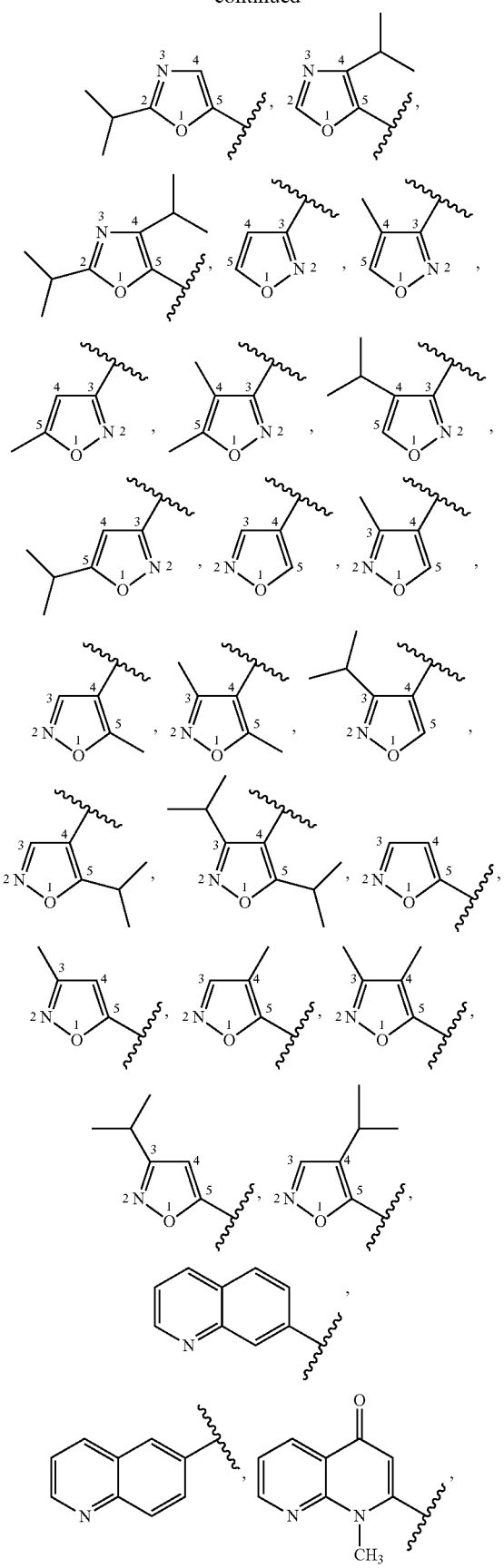

-continued
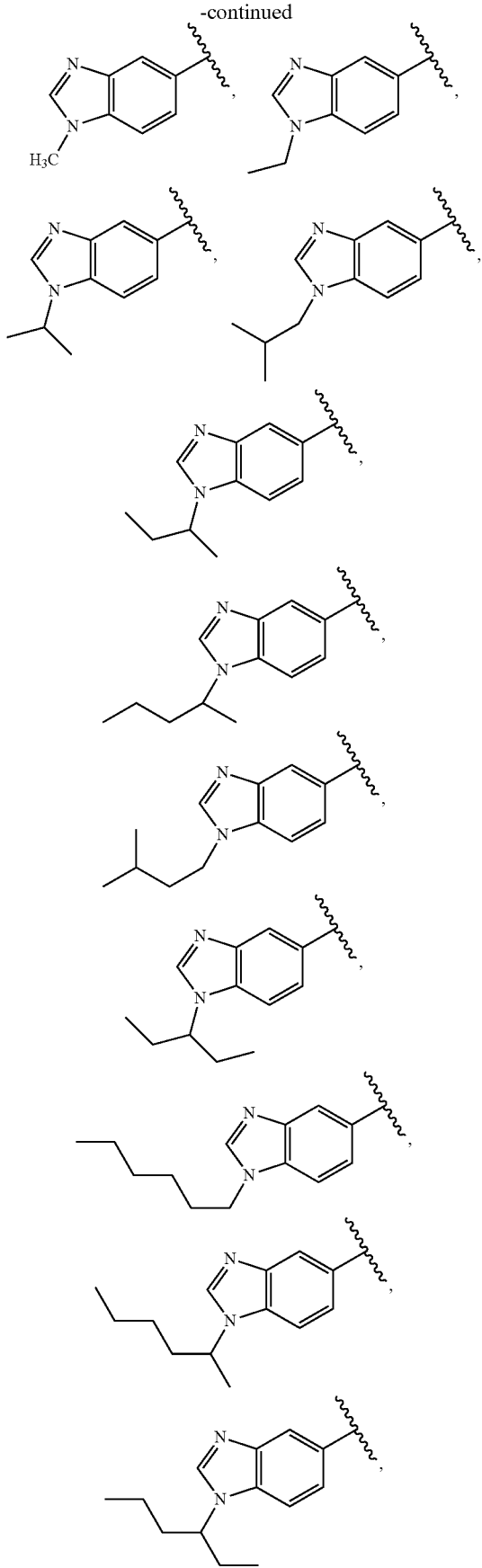
-continued
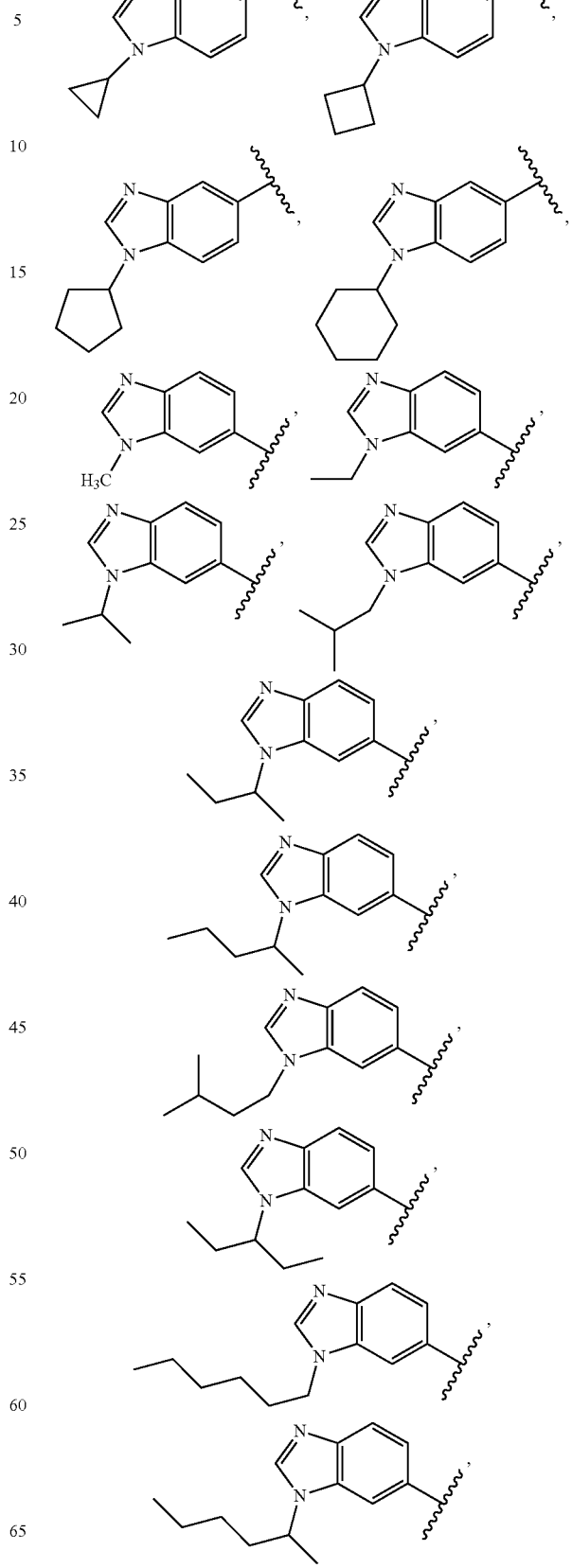

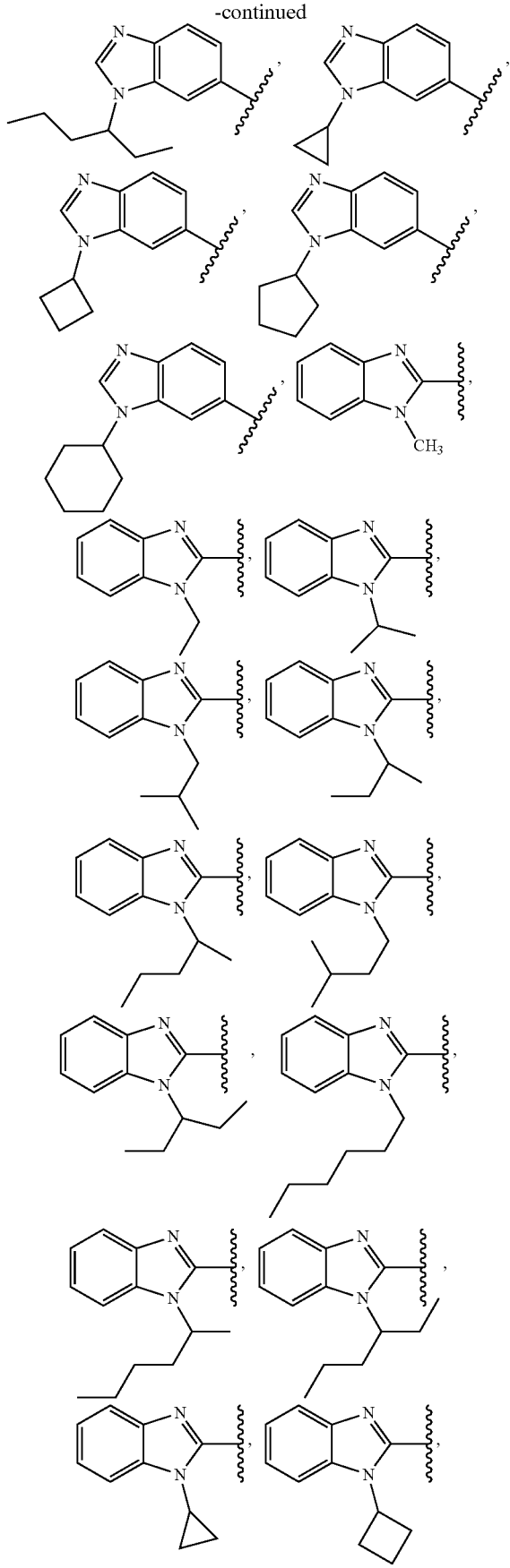
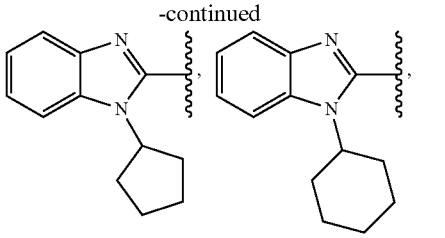
3. A method according to claim 1, wherein said scaffold is represented by general formula
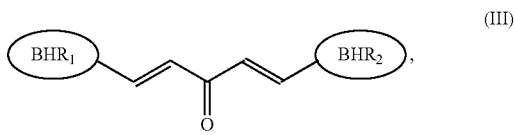

and said BHR₁ is
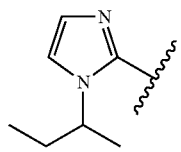 [SMILES: *c1nccn1C(C)CC]
and said BHR₂ is
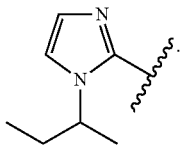 [SMILES: *c1nccn1C(C)CC]
4. A method according to claim 1, wherein said scaffold is represented by general formula
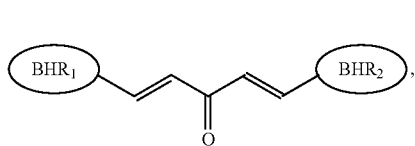 (III)
and said BHR₁ is
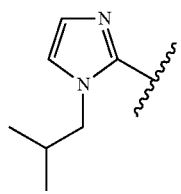 [SMILES: *c1nccn1CC(C)C]
and said BHR₂ is
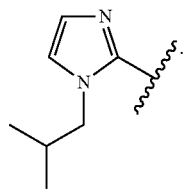
5. A method according to claim 1, wherein said scaffold is represented by general formula
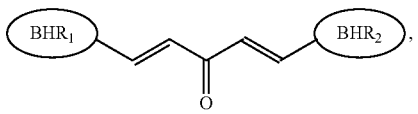 (III)
and said BHR₁ is
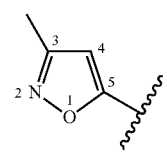
and said BHR₂ is
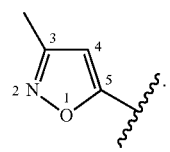
* * * * *